(12) United States Patent
Cardinale et al.

(10) Patent No.: US 10,610,345 B2
(45) Date of Patent: Apr. 7, 2020

(54) APPLICATOR INSTRUMENTS FOR DISPENSING SURGICAL FASTENERS HAVING ARTICULATING SHAFTS

(71) Applicant: Ethicon, Inc., Somerville, NJ (US)

(72) Inventors: Michael Cardinale, Morristown, NJ (US); Simon Cohn, Lebanon, NJ (US); Jianxin Guo, Livingston, NJ (US); Danial Paul Ferreira, Milford, CT (US)

(73) Assignee: Ethicon, Inc., Somerville, NJ (US)

( * ) Notice: Subject to any disclaimer, the term of this patent is extended or adjusted under 35 U.S.C. 154(b) by 348 days.

(21) Appl. No.: 15/271,639

(22) Filed: Sep. 21, 2016

(65) Prior Publication Data

US 2018/0078354 A1  Mar. 22, 2018

(51) Int. Cl.
*A61F 2/00* (2006.01)
*A61B 17/064* (2006.01)
(Continued)

(52) U.S. Cl.
CPC .......... *A61F 2/0063* (2013.01); *A61B 17/064* (2013.01); *A61B 17/0682* (2013.01);
(Continued)

(58) Field of Classification Search
CPC ................ A61B 17/068; A61B 17/682; A61B 2017/003; A61B 2017/00314;
(Continued)

(56) References Cited

U.S. PATENT DOCUMENTS 3,740,994 A  6/1973 DeCarlo, Jr.
4,471,780 A  9/1984 Menges et al.
(Continued)

FOREIGN PATENT DOCUMENTS

EP  0448284  9/1991
EP  2044893  4/2009
(Continued)

OTHER PUBLICATIONS

International Search Report issued in corresponding International Patent Application No. PCT/US2017/046849, dated Nov. 23, 2017, 6 pages.

(Continued)

*Primary Examiner* — Kathleen S Holwerda
*Assistant Examiner* — Kankindi Rwego

(57) ABSTRACT

An applicator instrument for dispensing surgical fasteners includes an elongated shaft having a proximal shaft section and a distal shaft section. The proximal shaft section includes an outer sheath and the distal shaft section includes a segmented member moveable between straight and articulated configurations. A handle is secured to the proximal shaft section, and an actuator is provided on the handle that is coupled with the outer sheath. An articulation band is disposed within the outer sheath and extends from the handle to the segmented member. The articulation band has a proximal end coupled with the actuator and a distal end attached to the segmented member. The actuator is moveable in a first direction for retracting the outer sheath, exposing the segmented member, and applying tension to the articulation band for moving the segmented member into the articulated configuration. The actuator is moveable in a second, opposite direction for extending the outer sheath, covering the segmented member, and releasing the tension on the articulation band to enable the segmented member to return to the straight configuration.

18 Claims, 19 Drawing Sheets

(51) Int. Cl.
  *A61B 17/068* (2006.01)
  *A61B 17/10* (2006.01)
  *A61B 17/00* (2006.01)

(52) U.S. Cl.
  CPC .... *A61B 17/10* (2013.01); *A61B 2017/00309* (2013.01); *A61B 2017/00314* (2013.01); *A61B 2017/00323* (2013.01); *A61B 2017/00336* (2013.01); *A61F 2002/0072* (2013.01)

(58) Field of Classification Search
  CPC ........... A61B 2017/00323; A61B 2017/07221; A61B 5/6855; A61B 17/00234; A61B 17/064; A61B 17/0682; A61B 17/10; A61B 2017/00292; A61B 2017/00296; A61B 2017/00305; A61B 2017/00309; A61B 2017/00318; A61B 2017/00327; A61B 2017/00331; A61B 2017/00336; A61B 2017/00334; A61B 2017/2905; A61B 2017/2927; A61F 2002/0072; A61F 2/0063; A61L 29/02; A61L 29/04
  USPC .................................. 600/141, 142; 606/139
  See application file for complete search history.

(56) References Cited

U.S. PATENT DOCUMENTS

| | | | |
|---|---|---|---|
| 4,478,220 A | 10/1984 | DiGiovanni et al. | |
| 5,042,707 A * | 8/1991 | Taheri | A61B 17/0684 227/175.1 |
| 5,203,864 A | 4/1993 | Phillips | |
| 5,246,156 A | 9/1993 | Rothfuss et al. | |
| 5,290,297 A | 3/1994 | Phillips | |
| 5,470,010 A | 11/1995 | Rothfuss et al. | |
| 5,549,637 A * | 8/1996 | Crainich | A61B 17/29 606/170 |
| 5,582,616 A | 12/1996 | Bolduc et al. | |
| 5,601,573 A | 2/1997 | Fogelburg et al. | |
| 5,669,926 A * | 9/1997 | Aust | A61B 17/32002 606/170 |
| 5,749,828 A | 5/1998 | Solomon et al. | |
| 5,810,882 A | 9/1998 | Boilduc et al. | |
| 5,830,221 A | 11/1998 | Stein et al. | |
| 5,833,700 A | 11/1998 | Fogelburg et al. | |
| 5,921,997 A | 7/1999 | Fogelburg et al. | |
| 6,743,239 B1 * | 6/2004 | Kuehn | A61B 17/0643 464/149 |
| 7,485,124 B2 | 2/2009 | Kuhns et al. | |
| 7,637,905 B2 * | 12/2009 | Saadat | A61B 1/0055 600/104 |
| 7,766,682 B1 | 8/2010 | Larkin | |
| 8,123,795 B1 * | 2/2012 | Knodel | A61B 17/068 623/1.11 |
| 8,277,375 B2 | 10/2012 | Danitz et al. | |
| 8,419,720 B1 | 4/2013 | Dawoodjee | |
| 8,567,033 B2 | 10/2013 | Macnamara | |
| 8,579,920 B2 | 11/2013 | Nering et al. | |
| 8,622,894 B2 | 1/2014 | Banik et al. | |
| 8,728,098 B2 | 5/2014 | Daniel et al. | |
| 8,728,099 B2 | 5/2014 | Cohn et al. | |
| 8,894,669 B2 | 11/2014 | Nering et al. | |
| 8,920,439 B2 | 12/2014 | Cardinale et al. | |
| 9,085,085 B2 | 7/2015 | Danitz et al. | |
| 9,144,370 B2 | 9/2015 | Kato et al. | |
| 9,204,783 B2 | 12/2015 | Kappel et al. | |
| 2009/0312773 A1 * | 12/2009 | Cabrera | A61B 17/0469 606/144 |
| 2011/0257637 A1 * | 10/2011 | Timmerman | A61B 17/00234 606/1 |
| 2013/0150831 A1 * | 6/2013 | Griffiths | A61B 17/00 606/1 |
| 2013/0158526 A1 * | 6/2013 | Frank | A61B 17/29 606/1 |
| 2014/0336675 A1 * | 11/2014 | Menn | A61B 17/1285 606/142 |
| 2017/0007224 A1 * | 1/2017 | Sholev | A61M 25/0136 |

FOREIGN PATENT DOCUMENTS

| | | |
|---|---|---|
| EP | 2949262 | 12/2015 |
| WO | 2011127137 | 10/2011 |
| WO | 2013179106 | 12/2013 |
| WO | 2013192431 | 12/2013 |
| WO | 2015004667 | 1/2015 |
| WO | 2015125140 | 8/2015 |

OTHER PUBLICATIONS

Written Opinion issued in corresponding International Patent Application No. PCT/US2017/046849, dated Nov. 23, 2017, 9 pages.

* cited by examiner

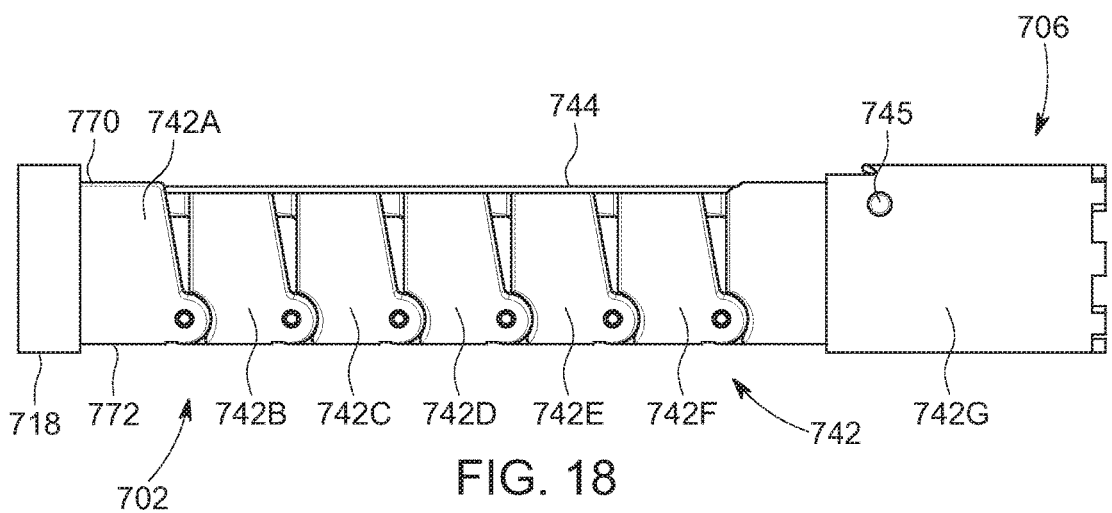
FIG. 18
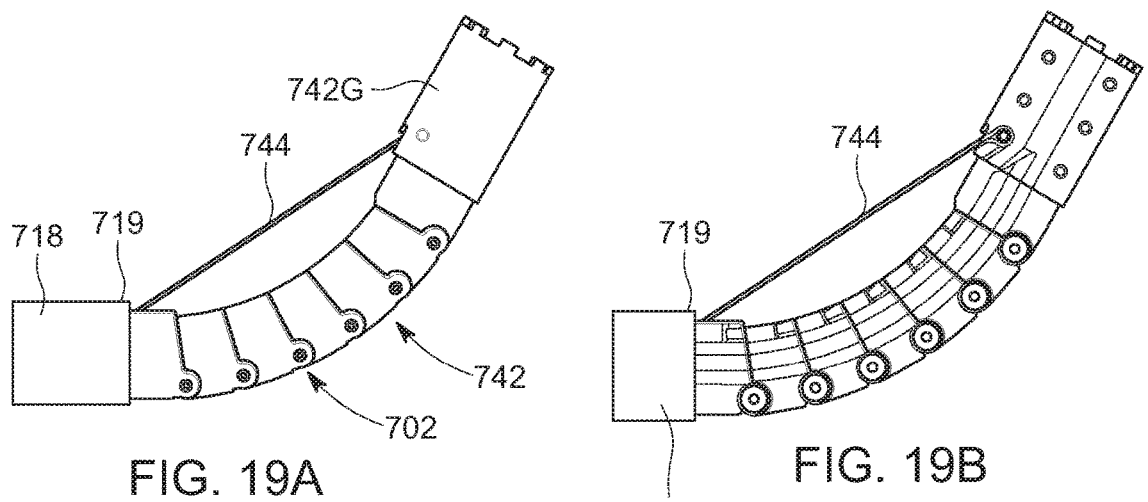
FIG. 19A
FIG. 19B
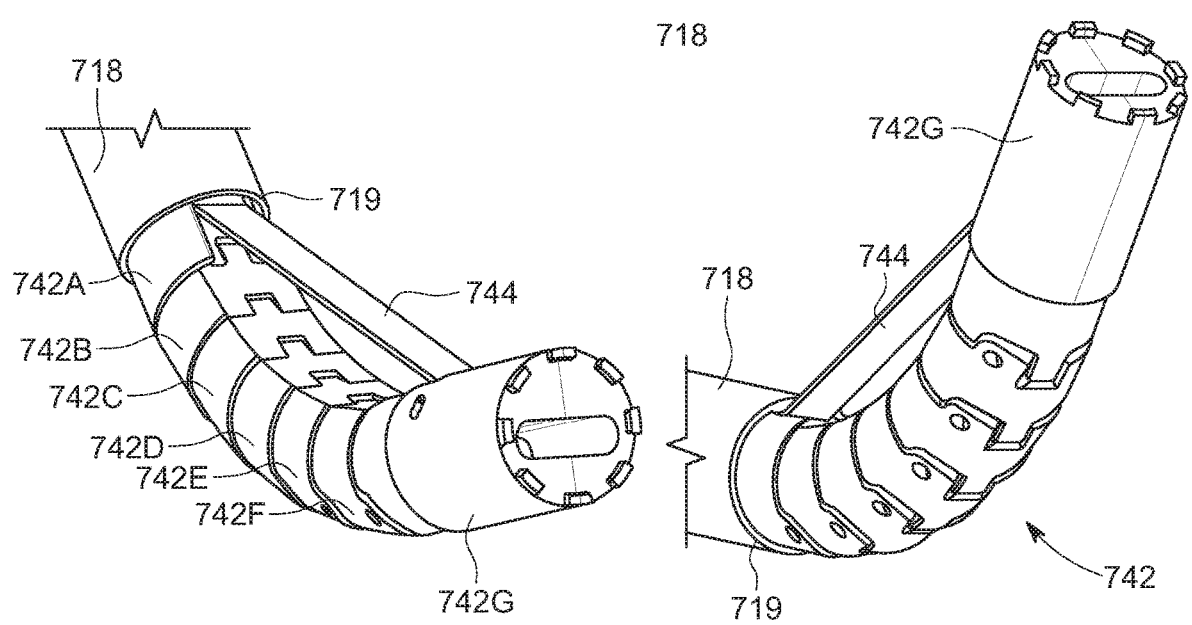
FIG. 19C
FIG. 19D

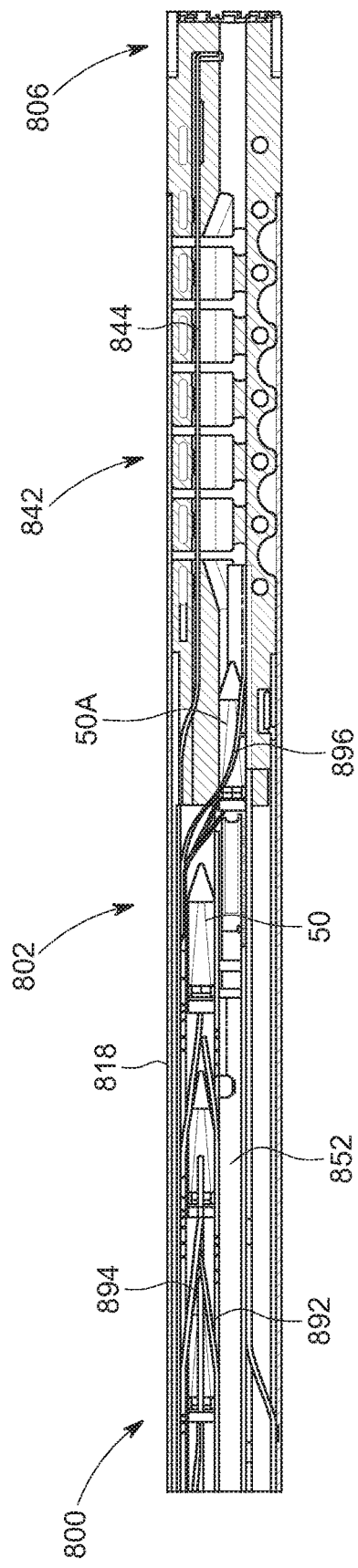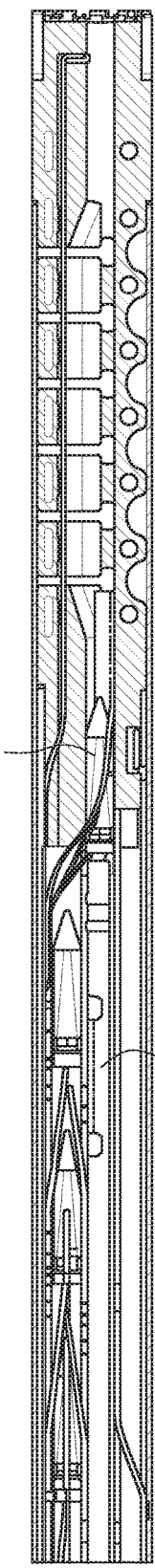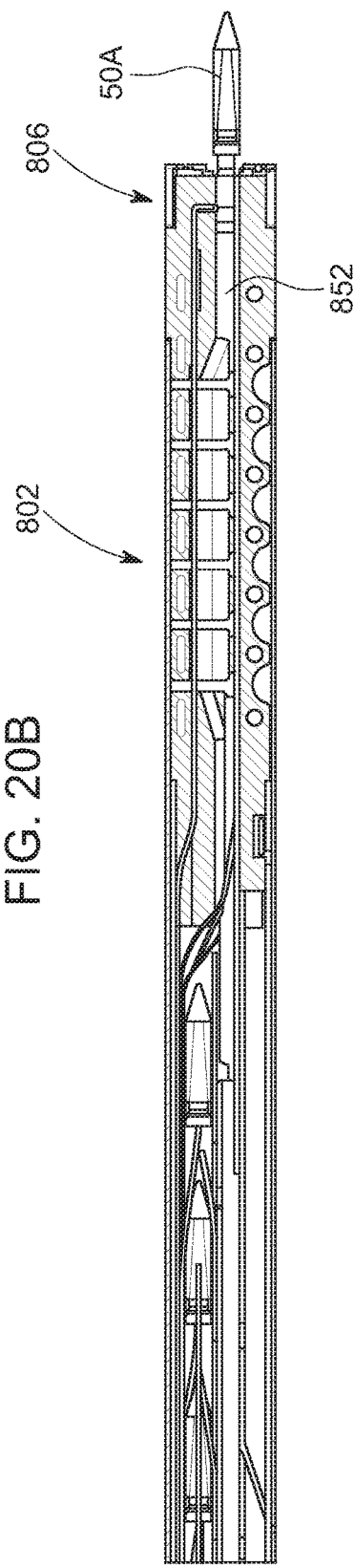

APPLICATOR INSTRUMENTS FOR DISPENSING SURGICAL FASTENERS HAVING ARTICULATING SHAFTS

BACKGROUND OF THE INVENTION

Field of the Invention

The present patent application generally relates to applicator instruments for dispensing surgical fasteners, and more specifically relates to applicator instruments, systems and methods that use articulating shafts for deploying surgical fasteners.

Description of the Related Art

A hernia is a condition where a small loop of bowel or intestine protrudes through a weak place or defect within the abdominal muscle wall or groin of a patient. This condition commonly occurs in humans, particularly males. Hernias of this type may result from a congenital defect whereby the patient is born predisposed with this condition, prior abdominal surgery, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

U.S. Pat. No. 3,740,994 to DeCarlo Jr. discloses a reciprocating feeding mechanism that indexes a plurality of staples or clips, and readies them for discharge by reciprocating one of a pair of opposing leaf spring assemblies. The staples reside serially within a guide rail with a fixed leaf spring assembly extending into the plane of the guide rail. A reciprocating leaf spring assembly may extend inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Pat. No. 7,485,124, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, an absorbable tack with minimum profile that can be applied laparoscopically is needed.

Commonly assigned U.S. Pat. No. 8,920,439, the disclosure of which is hereby incorporated by reference herein, discloses an applicator instrument for dispensing surgical fasteners having an elongated shaft with a proximal shaft section and a distal shaft section. The applicator instrument has an articulation controller coupled with the distal shaft section for selectively changing the angle between the distal shaft section and the proximal shaft section. The articulation controller has at least one flexible linkage extending through the shaft and has a proximal end connected with an actuator and a distal end connected with the distal shaft section. The actuator is mounted on a housing for sliding between proximal and distal ends of the housing for moving the at least one flexible linkage in proximal and distal directions. Surgical fasteners are disposed within elongated shaft for being dispensed one at a time from the distal end of the elongated shaft.

In spite of the above advances, intra-operative conditions during laparoscopic surgery remain challenging for the surgeon. There remains a need for applicator instruments for dispensing surgical fasteners that have improved ergonomics, that enable ipsillateral (same side) mesh tensioning, and that provide maneuverability both inside and outside of a body cavity. There also remains a need for applicator instruments for dispensing surgical fasteners that have optimal distal shaft strength when the shaft is articulated, and that provide pre-defined articulation angles for simplifying the device complexity and the user experience.

SUMMARY OF THE INVENTION

In one embodiment, an applicator instrument for dispensing surgical fasteners has an articulating shaft. In one embodiment, the applicator instrument has a proximal shaft section having a proximal end, a distal end, and a longitudinal axis, a handle attached to the proximal end of the proximal shaft section, a segmented member, an articulation band within the segmented member, and an outer sheath. The applicator instrument has an articulation actuator that retracts the outer sheath and tensions the articulation band to force the articulation of the segmented member.

In one embodiment, the segmented member may be a notched plastic component, a notched metal component or tube, or multiple independent members (e.g., links) that are joined together.

In one embodiment, surgical fasteners may be disposed within the proximal shaft section and travel through the segmented member when the instrument is fired. In one embodiment, the elongated shaft of the applicator instrument may toggle between a straight configuration and a fixed angle relative to the proximal shaft section, preferably between about 30-60 degrees.

In one embodiment, when the outer sheath retracts, gripping features on the distal end of the instrument may be exposed or expand outward for providing a gripping feature.

In one embodiment, the articulation band rests above the segmented member and may form a bee-line when the segmented member is articulated. In one embodiment, locating the articulation band above the segmented member shields the segments or links from being damaged by the cannula and also may improve the rigidity of the articulated configuration.

Although the applicator instrument disclosed herein is not limited by any particular theory of operation, it is believed that its unique articulating structure can improve the following intra-operative conditions during hernia surgery: 1) Ergonomics, 2) Ipsillateral (same side) mesh tensioning, 3) Maneuverability, both inside and outside the body cavity, 4) Visualization of the fixation site, and 5) a straight configuration that is perfectly straight and rigid similar to any non-articulating instrument.

In one embodiment, toggling between 0 degrees and a pre-defined articulation angle may be sufficient for all scenarios, greatly simplifying the device complexity and the user experience.

In one embodiment, the applicator instrument may be more robust when locked at the desired angle. In the straight position/configuration, the outer sheath preferably provides rigidity. In the articulated position/configuration, the articulation band provides rigidity when the segmented member reaches a fully collapsed, solid height.

In one embodiment, articulation of the segmented member may be effectively achieved using only a single articulation band, which frees space within the housing and simplifies the timing compared to conventional two band systems. Since rigidity is only required at the straight and articulated positions, the interim steps of retracting the outer sheath and tensioning the articulation band do not require precise timing. It is also easier to dial in the tension on such a system.

In one embodiment, the segmented member is made of independent links that allow for manufacturability and avoid yielding.

In one embodiment, an applicator instrument for dispensing surgical fasteners preferably includes an elongated shaft having a proximal shaft section and a distal shaft section, the proximal shaft section including an outer sheath and the distal shaft section including a segmented member disposed within a distal end of the outer sheath. The segmented member is desirably moveable between a straight configuration and an articulated configuration. In one embodiment, the applicator instrument has a handle secured to the proximal shaft section, and an actuator, such as a lever, is provided on the handle is being coupled with the outer sheath for moving the outer sheath in proximal and distal directions along an axis.

In one embodiment, an articulation band is disposed within the outer sheath. The articulation band desirably extends from the handle to the segmented member, with the articulation band having a proximal end coupled with the actuator (e.g., a lever) and a distal end attached to the segmented member. In one embodiment, the actuator is moveable in a first direction (e.g., proximally) for moving the outer sheath in a proximal direction along the axis to expose a portion of the segmented member and applying tension to the articulation band for moving the segmented member into the articulated configuration. In one embodiment, the actuator is moveable in a second, opposite direction for moving the outer sheath in a distal direction along the axis to cover the portion of the segmented member and to release the tension on the articulation band to enable the segmented member to return to the straight configuration.

In one embodiment, the segmented member may be a cannula made of a compliant material that normally springs back to the straight configuration. As such, if the cannula is bent under force, the cannula normally reverts back to a straight configuration when the force is released. In one embodiment, the cannula is made of plastic or metal. In one embodiment, the cannula has notches that divide the segmented member into links that are interconnected and moveable relative to one another.

In one embodiment, the segmented member includes a distal link that is located at a distal-most end of the elongated shaft and a series of proximal links that are proximal to the distal link. In one embodiment, the distal end of the articulation band is affixed to the distal link of the segmented member. In one embodiment, the articulation band desirably passes through the proximal links adjacent upper ends of the proximal links. In one embodiment, the articulation band passes above the upper ends of the proximal links (i.e., over or outside the proximal links).

In one embodiment, the proximal links have a first length and the distal link has a second length that is greater than the first length. In one embodiment, the second length of the distal link is greater than the combined length of a surgical fastener and an insertion fork carrying the surgical fastener, which provides a straight path for the surgical fastener and insertion fork immediately adjacent to the distal-most end of the elongated shaft.

In one embodiment, the segmented member has a series of links having lower ends that are hingedly connected to one another, whereby the distal end of the articulation band is affixed to a distal-most one of the links. In one embodiment, the links include proximal links that are proximal to the distal-most one of the links, whereby each proximal link has a lower end including a proximal connection flange and a distal connection flange for forming a hinge connection, and whereby each proximal link has an upper end including a tongue and groove structure for engaging the tongue and groove structure on adjacent links.

In one embodiment, the applicator instrument has a firing system disposed in the handle. The firing system preferably includes a firing rod that extends through the proximal and distal shaft sections of the elongated shaft. In one embodiment, the firing rod moves in distal and proximal directions during a firing cycle. An actuator may be coupled with the handle for activating the firing system. In one embodiment, a plurality of surgical fasteners are disposed in the elongated shaft, whereby a leading one of the surgical fasteners is dispensed during each firing cycle. In one embodiment, the fasteners are singulated from the handle end and are not disposed in the elongated shaft.

In one embodiment, the firing rod has a distal end that is flexible for bending when the segmented member is in the articulated configuration. In one embodiment, the distal end of the firing rod is substantially straight when the segmented member is in the straight configuration and the firing rod is adapted to bend when the segmented member is in the articulated configuration.

In one embodiment, an applicator instrument for dispensing surgical fasteners preferably has an elongated shaft with a proximal shaft section and a distal shaft section, the proximal shaft section including a rigid outer sheath and the distal shaft section including a segmented member disposed within a distal end of the outer sheath. In one embodiment, the segmented member preferably has a series of links that are flexibly interconnected for enabling the segmented member to move between a straight configuration and an articulated configuration.

In one embodiment, a handle is secured to the proximal shaft section, and an actuator (e.g., a lever) is provided on the handle and coupled with the outer sheath for moving the outer sheath in proximal and distal directions along an axis.

In one embodiment, an articulation band is disposed within the outer sheath that extends from the handle to the segmented member. The articulation band preferably has a proximal end coupled with the actuator and a distal end attached to a distal-most one of the links. In one embodiment, the actuator is moveable in a first direction for moving the outer sheath in a proximal direction along the axis to expose the links of the segmented member and applying tension to the articulation band for moving the segmented member into the articulated configuration. In one embodiment, the actuator is moveable in a second, opposite direction for moving the outer sheath in a distal direction along the axis to cover the links of the segmented member and releasing the tension on the articulation band for enabling the segmented member to return to the straight configuration. In one embodiment, the compliancy of the segmented member returns the segmented member to the straight configuration once the tension on the articulation band is released.

In one embodiment, the links of the segmented member preferably have lower ends with hinge connections. In one embodiment, the links have upper ends with tongue and groove structure for engaging the tongue and groove structure of an adjacent link. The tongue and groove structure provides a keying effect whereby the segmented member is stable and resists twisting when fully articulated.

In one embodiment, the applicator instrument preferably has a firing system disposed in the handle. The firing system may have a firing rod that extends through the proximal and distal shaft sections of the elongated shaft. In one embodiment, the firing rod moves in distal and proximal directions during a firing cycle. In one embodiment, the firing rod has a distal end that is flexible for bending when the segmented member is in the articulated configuration. In one embodiment, the applicator instrument has an actuator (e.g., a trigger) coupled with the handle for activating the firing system.

In one embodiment, a plurality of surgical fasteners are disposed in the elongated shaft, and a leading one of the surgical fasteners is dispensed during each firing cycle (e.g., each time the trigger is pulled).

In one embodiment, a method of repairing a hernia defect preferably includes inserting a mesh into a patient's abdominal cavity, and placing the mesh over a hernia defect. The method may include providing an applicator instrument for dispensing surgical fasteners, the applicator instrument including a handle and an elongated shaft extending from a distal end of the handle, the elongated shaft having a proximal shaft section and a distal shaft section, the proximal shaft section including an outer sheath and the distal shaft section including a segmented member disposed within a distal end of the outer sheath, whereby the segmented member is moveable between a straight configuration and an articulated configuration.

In one embodiment, the method includes providing an actuator, such as a lever, on the handle that is coupled with the outer sheath for moving the outer sheath in proximal and distal directions along an axis. In one embodiment, the method may include providing an articulation band within the outer sheath that extends from the handle to the segmented member, the articulation band having a proximal end coupled with the actuator and a distal end attached to the segmented member. Surgical fasteners may be disposed in the elongated shaft.

In one embodiment, with the segmented member in the straight configuration, the distal shaft section of the elongated shaft may be inserted into the patient's abdominal cavity. The actuator may be moved in a first direction for moving the outer sheath in a proximal direction along the axis to expose a portion of the segmented member and applying tension on the articulation band for moving the segmented member into the articulated configuration. A distal-most end of the distal shaft section may be abutted against the mesh, and at least one of the surgical fasteners may be dispensed from the distal-most end of the distal shaft section, through the mesh, and into an abdominal wall of the patient for securing the mesh to tissue.

In one embodiment, the actuator may be moved in a second, opposite direction for moving the outer sheath in a distal direction along the axis to cover the portion of the segmented member and releasing the tension on the articulation band to enable the segmented member to return to the straight configuration.

These and other preferred embodiments of the present invention will be described in more detail below.

BRIEF DESCRIPTION OF THE DRAWING

FIG. 18 shows an applicator instrument with an elongated shaft having a segmented member in a straight configuration, in accordance with one embodiment.

FIGS. 19A-19D show the applicator instrument of FIG. 18 with the segmented member in an articulated configuration, in accordance with one embodiment.

FIGS. 20A-20O show a firing system for an applicator instrument in a straight configuration, in accordance with one embodiment.

DETAILED DESCRIPTION OF PREFERRED EMBODIMENTS

Figure 4A:
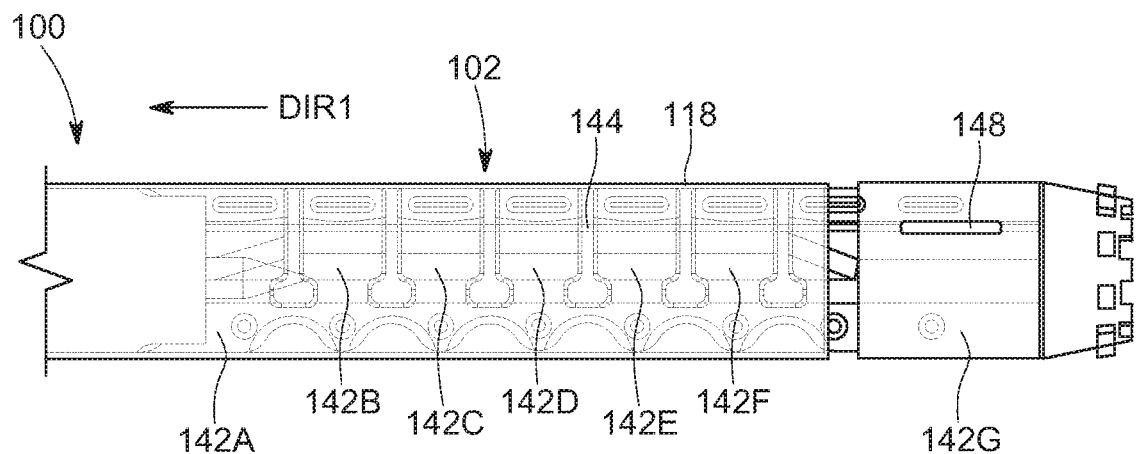
FIGS. 4A-4C and 4C-1 show an elongated shaft for an applicator instrument for dispensing surgical fasteners, in accordance with one embodiment.
Figure 4B:
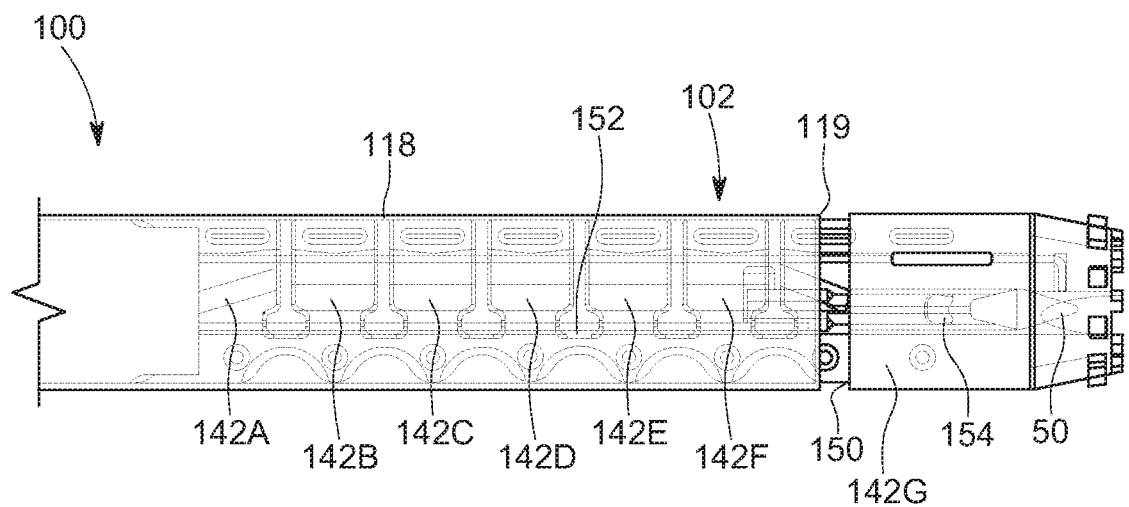
Figure 4C:
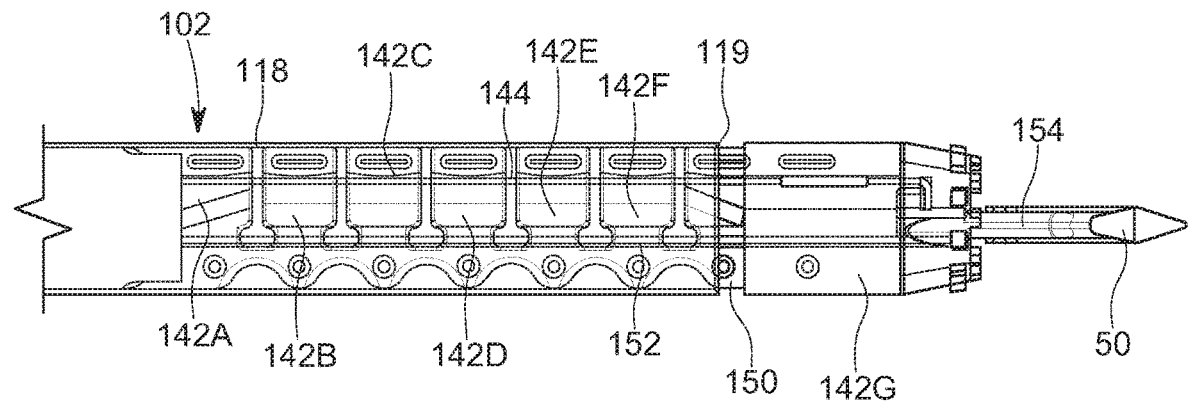
Figures 1, 4C:
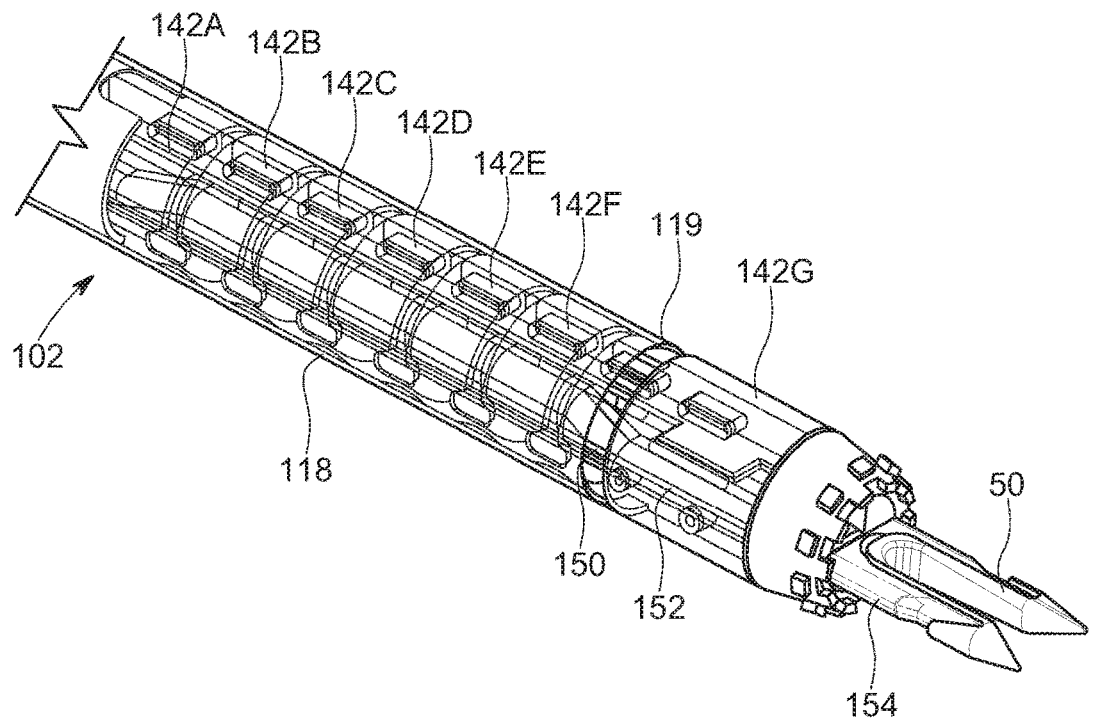

Referring to FIG. 1, in one embodiment, an applicator instrument 100 for dispensing surgical fasteners preferably includes an elongated shaft 102 having a proximal end 104, a distal end 106, and an elongated axis $A_1$ that extends between the proximal and distal ends 104, 106. In one embodiment, the applicator instrument 100 includes a handle 108 secured to the proximal end 104 of the elongated shaft 102. The handle 108 desirably has a hand grip 110 and a trigger 112 that may be squeezed to commence a firing cycle for dispensing a surgical fastener from the distal end 106 of the elongated shaft 102. In one embodiment, the trigger may be replaced by an actuator that commences a firing cycle for dispensing a surgical fastener.

Figure 1A:
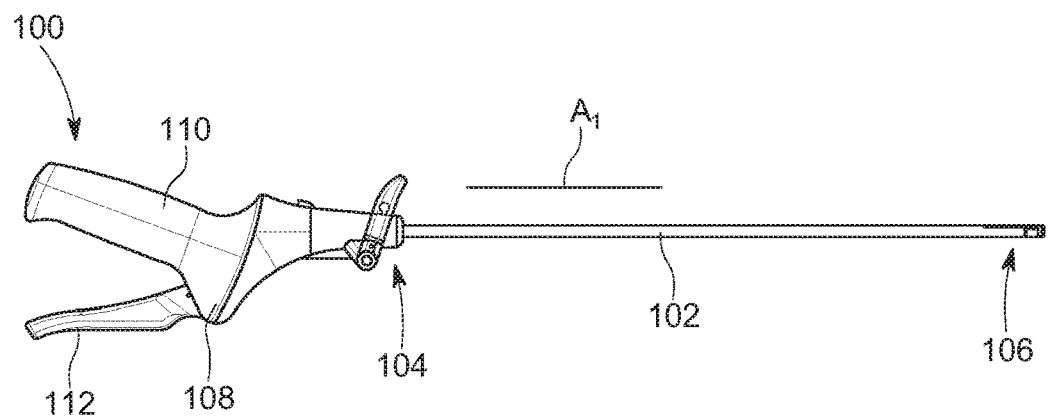
FIGS. 1A-1C show an applicator instrument for dispensing surgical fasteners, in accordance with one embodiment.
Figure 1B:
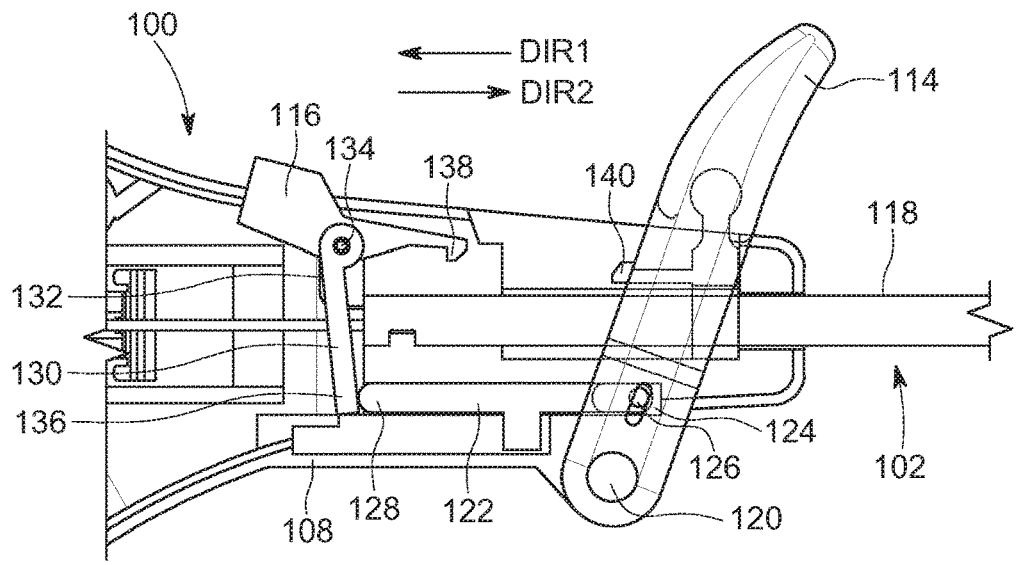

Referring to FIGS. 1A and 1B, in one embodiment, the applicator instrument 100 includes an actuator such as an articulation lever 114 that is coupled with the elongated shaft 102 for articulating a distal end of the instrument as will be described in more detail herein. The applicator instrument 100 also includes a release 116 that is accessible on the handle 108 and that may be engaged for automatically returning the elongated shaft 102 from an articulated configuration to a straight configuration. In one embodiment, surgical fasteners may be dispensed from the distal end 106 of the elongated shaft 102 with the elongated shaft in the straight configuration shown in FIG. 1C or an articulated configuration. In one embodiment, the elongated shaft provides rigidity of the distal end when in the straight configuration but not when in the articulated configuration.

Figure 1C:

Referring to FIGS. 1B and 1C, in one embodiment, the elongated shaft 102 includes an outer sheath 118 that is connected with the actuator 114 (e.g., an articulation lever) on the handle 108. The outer sheath may be made of a durable, biocompatible material such as stainless steel. In one embodiment, a lower end of the articulation lever 114 is pivotally connected with the body of the handle 108 via a pivot 120. The applicator instrument 100 also includes an articulation tensioner 122 having a proximal end 124 connected with the articulation lever 114 via a pin 126. The articulation tensioner 122 has a proximal end 128 adapted to engage a lever 130. In one embodiment, the lever 130 has an upper end 132 that is pivotally connected with the body of the handle via a pin 134 and a free, lower end 136 that is adapted to be contacted by the proximal end 128 of the articulation tensioner 122. In one embodiment, when the articulation tensioner 122 moves proximally (i.e., to the left in FIGS. 1A and 1B), the lower end 136 of the lever 130 is pushed in a clockwise direction as it pivots around the pin 134.

In one embodiment, the applicator instrument 100 includes the release 116 having a catch 138 that is adapted to engage a catch 140 connected to the articulation lever 114. In one embodiment, a torsional spring provides a clockwise torque on the release 116. In one embodiment, when the lever is pulled in the proximal direction designated DIR1, the catch 140 coupled with the lever engages the catch 138 on the release 116 for holding the lever 114 in a retracted position. The lever 114 will remain in the retracted position until the release 116 is depressed for decoupling the catch 138 from the catch 140, whereupon, the lever will be free to move in the distal direction designated DIR2. In one embodiment, a compression spring biases the articulation tensioner 122 toward the distal direction designated DIR2.

Figure 10:
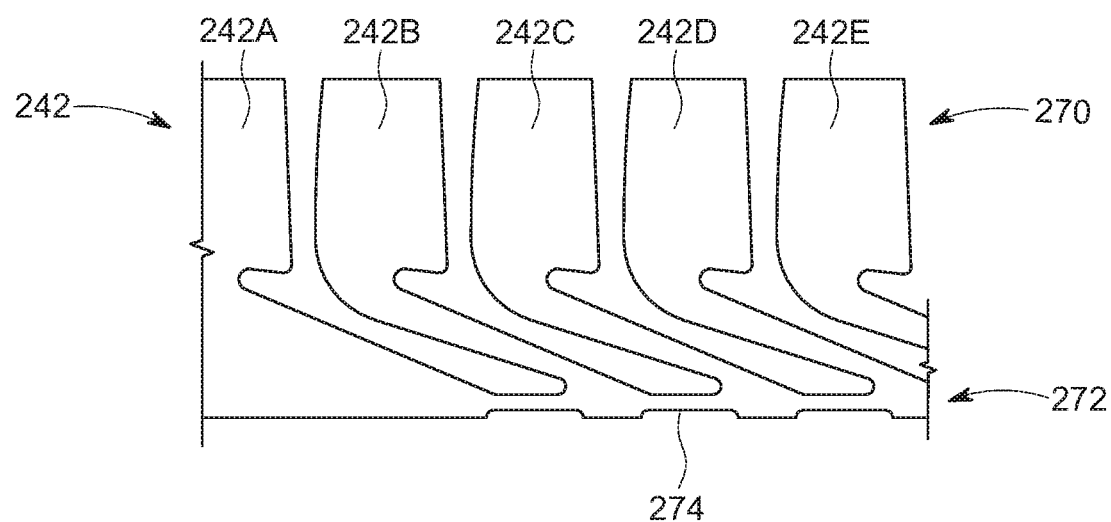
FIG. 10 shows a segmented member for an applicator instrument, in accordance with one embodiment.

Referring to FIG. 10, in one embodiment, the elongated shaft 102 of the applicator instrument includes the outer sheath 118 that is coupled with the articulation lever 114 (FIG. 1B) and a segmented member 142 located at the distal end 106 of the shaft 102. In one embodiment, the segmented member 142 is located inside the outer sheath 118 and the lever 114 is used to move the outer sheath 118 proximally and distally relative to the segmented member 142. In one embodiment, when the articulation lever 114 is pulled toward the proximal end of the handle, the outer sheath moves proximally in the direction designated DIR1 for exposing the segmented member 142 as the outer sheath 118 is retracted. An articulation band (not shown) having a distal end connected to the segmented member and a proximal end coupled with the lever 130 is tensioned as the lever 130 moves clockwise, which causes the segmented member 142 to articulate (e.g., bend or curve), as will be described in more detail herein.

Referring to FIGS. 1B and 1C, in one embodiment, in order to articulate the distal end 106 of the elongated shaft 102, the articulation lever 114 is pulled in the proximal direction designated DIR1. As the articulation lever 114 pivots in a counter clockwise direction, the connection between the pin 126 and the proximal end 124 of the articulation tensioner 122 moves the articulation tensioner in the proximal direction. As the articulation tensioner moves proximally, the proximal end 128 of the articulation tensioner engages the lower end 136 of the lever 130 for rotating the lower end 136 in a clockwise direction. As the lever 114 moves proximally, the outer sheath 118 of the elongated shaft 102 is retracted. As the lower end 136 of the lever 130 rotates clockwise, tension is applied to the articulation band which forces articulation of the segmented member 142. As the articulation lever 114 is pulled proximally, the catch 140 on the lever 114 engages the catch 138 on the release 116 to hold the lever 114 in a rearward position. In order to release the lever 114 and allow the outer sheath 118 of the elongated shaft 102 to move distally, the release 116 may be depressed for disengaging the catch 138 from the catch 140 on the articulation lever 114 which frees the outer sheath 118 to move in a distal direction.

Figure 2:
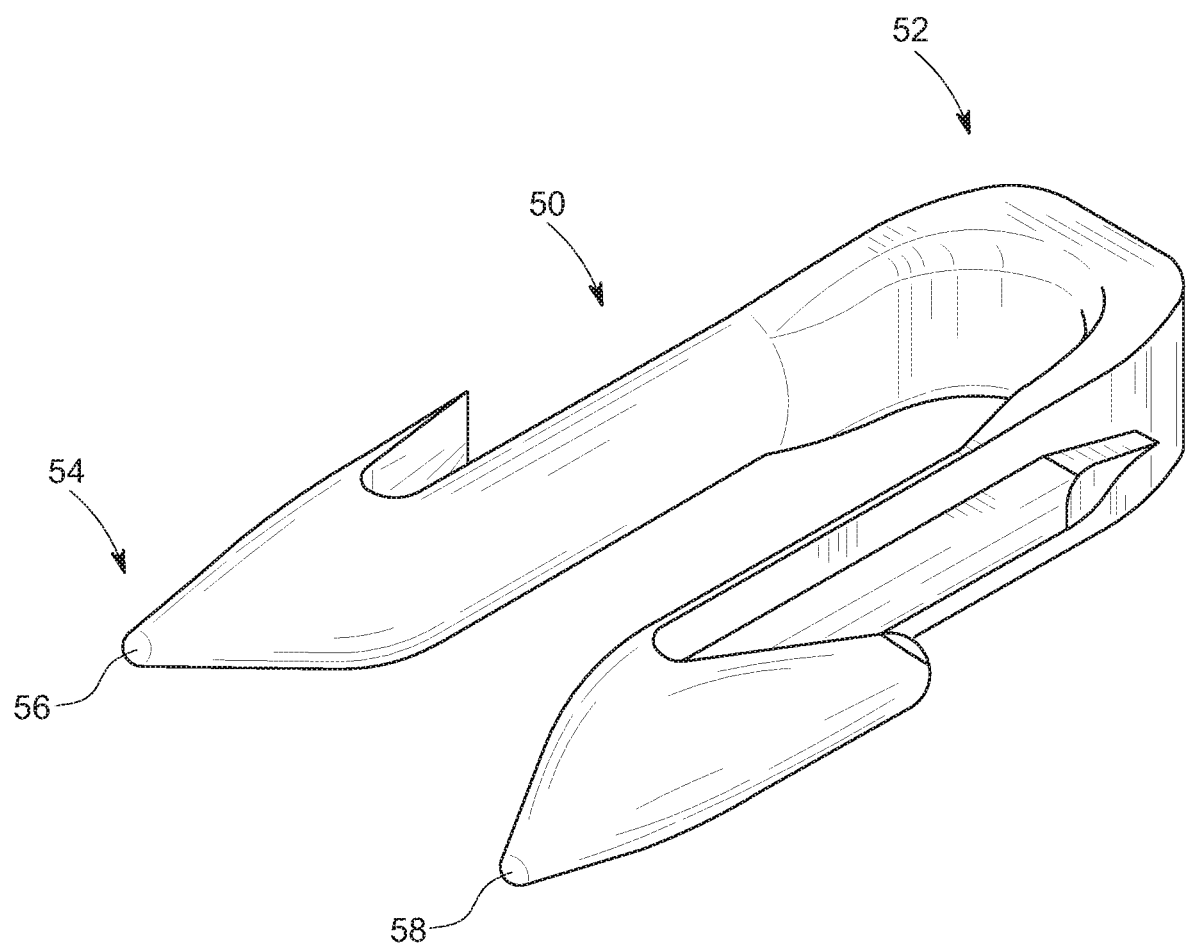
FIG. 2 shows a surgical fastener that is dispensed by the applicator instrument of FIGS. 1A-1C, in accordance with one embodiment.

In one embodiment, a series of surgical fasteners are pre-loaded into the elongated shaft 102 of the applicator instrument 100. Referring to FIG. 2, in one embodiment, a single surgical fastener 50 includes a proximal end 52 and a distal end 54 having insertion tips 56, 58 that are spaced from one another for capturing mesh fibers between the tapered ends. In one embodiment, the surgical fastener 50 has one or more of the features disclosed in commonly assigned U.S. Pat. Nos. 8,579,920; 8,728,098; 8,728,099; 8,894,669; and 8,920,439, the disclosures of which are hereby incorporated by reference herein. In one embodiment, a single surgical fastener is dispensed from the distal end of the elongated shaft each time the trigger is pulled. In one embodiment, during each firing cycle, a lead surgical fastener is dispensed and the trailing surgical fasteners are advanced one position closer to the distal end of the elongated shaft.

Figure 3A:
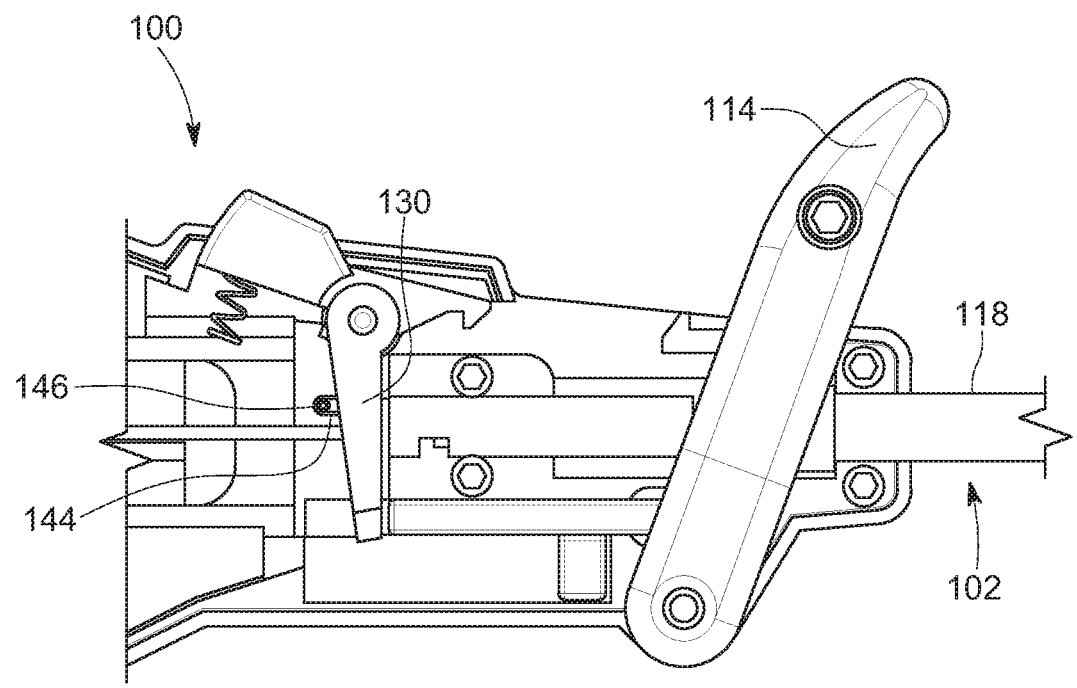
FIGS. 3A and 3B show an applicator instrument for dispensing surgical fasteners having an actuator for moving an outer sheath, in accordance with one embodiment.
Figure 3B:
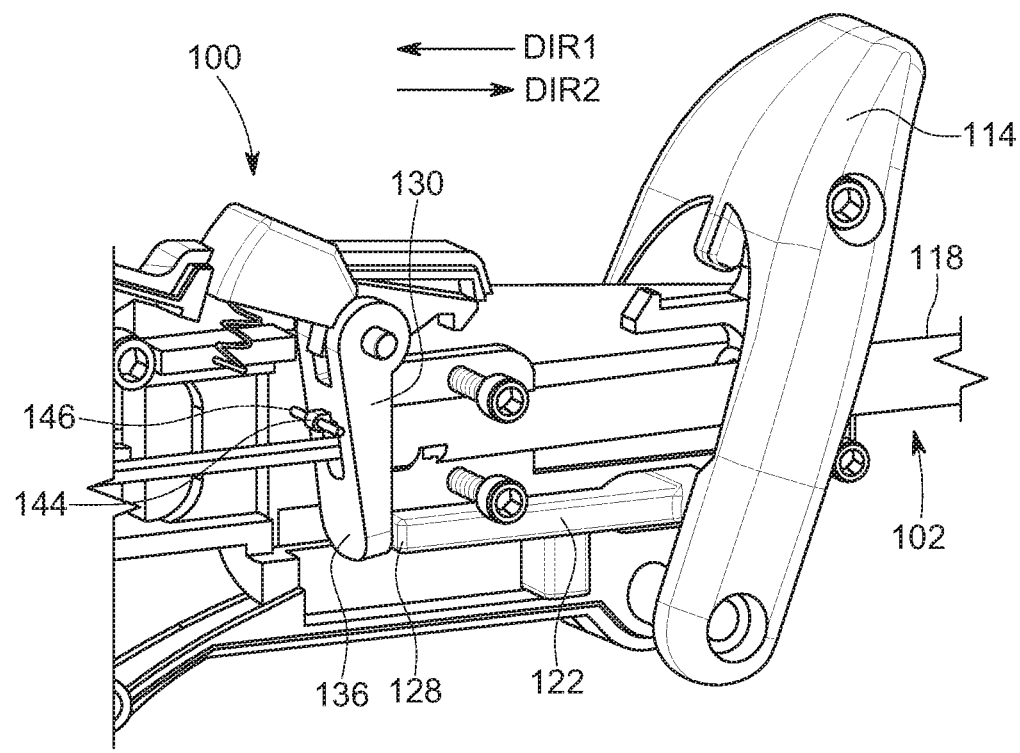

Referring to FIGS. 3A and 3B, in one embodiment, the applicator instrument 100 includes an articulation band 144 having a proximal end that is coupled with the lever 130 via a pin 146. A distal end of the articulation band 144 is connected with the segmented member 142 (FIG. 10). In one embodiment, as the articulation lever 114 is pulled in the proximal direction designated DIR1, the articulation tensioner 122 moves proximally whereupon the proximal end 128 of the articulation tensioner 122 engages the lower end 136 of the lever 130. Further proximal movement of the articulation tensioner 122 causes the lower end 136 of the lever 130 to pivot in a clockwise direction, which, in turn, applies tension to the articulation band 144 via the pin 146. The tension in the articulation band will pull the segmented member proximally for articulating the segmented member.

In one embodiment, as the articulation lever 114 moves distally in a direction designated DIR2, the articulation tensioner 122 moves distally which enables the lower end 136 of the lever 130 to rotate in a counter clockwise direction for releasing the tension on the articulation band 144. As the tension is released in the articulation band 144, the segmented member will return from the articulated configuration to the straight configuration.

Referring to FIG. 4A, in one embodiment, the elongated shaft 102 includes the outer sheath 118 that is adapted to move in proximal and distal directions via its linkage with the articulation lever 114 (FIGS. 3A and 3B). The elongated shaft 102 includes a segmented member 142 having a series of proximal links 142A-142F, and a distal link 142G having a greater length than the proximal links 142A-142F. In one embodiment, the distal link 142G has a length L1 that is greater than the combined length of the surgical fastener 50 when it is held by an insertion fork at a distal end of a firing rod as will be described in more detail herein. The applicator instrument includes the articulation band 144 that passes through upper ends of the proximal links 142A-142F. The articulation band 144 is not fixed to the proximal links and is able to move proximally and distally relative to the proximal links. The distal end 148 of the articulation band 144 is fixed to the distal link 142G. In one embodiment, as the outer sheath is retracted for exposing the distal link 142G and at least some of the proximal links 142A-142F, tension is applied to the articulation band 144 for pulling the upper end of the distal link 142G in the distal direction designated DIR1 and articulating the proximal links 142A-142F of the segmented member 142. In one embodiment, movement of the outer sheath 118 and the articulation band 144 is coordinated and synchronized using linkages so that proximal movement of the outer sheath and tensioning of the articulation band occurs simultaneously, and so that distal movement of the outer sheath and untensioning of the articulation band occurs simultaneously.

Referring to FIGS. 4B, 4C, and 4C-1, in one embodiment, the applicator instrument 100 may be fired with the elongated shaft 102 in a straight, non-articulated configuration or in an articulated configuration. With the applicator instrument in the straight configuration, the outer sheath 118 is extended in a distal-most position for substantially covering the proximal links 142A-142F of the segmented member 142. In the straight configuration, at least a portion of the distal link 142G may project beyond the distal-most end 119 of the outer sheath 18. In one embodiment, the distal-most end 119 of the outer sheath 118 may be spaced proximal to a shoulder 150 provided adjacent a proximal end of the distal link 142G.

In one embodiment, the applicator instrument 100 preferably includes a firing rod 152 having an insertion fork 154 secured to a distal end thereof for firing a surgical fastener 50 from the distal end of the elongated shaft 102. During a firing cycle, the firing rod 152 is preferably adapted to move in distal and proximal directions through the outer sheath 118 and the segmented member 142 of the elongated shaft 102.

FIGS. 4C and 4C-1 show the firing rod 152 is a fully extended position with the insertion fork 154 distal to a distal-most end of the distal link 142G of the segmented member 142. The articulation band 144 is in a lower or untensioned state so that the segmented member 142 is straight and extends along the longitudinal axis $A_1$ of the outer sheath 118 of the elongated shaft 102. In one embodiment, the distal-most end 119 of the outer sheath 118 engages the proximal end of the distal link 142G for enhancing the rigidity of the distal end of the elongated shaft 102.

The insertion fork 154 controls the orientation of the surgical fastener 50 as the surgical fastener is inserted into tissue and/or mesh. In one embodiment, a plurality of surgical fasteners are disposed within a proximal end of the elongated shaft 102 and a single, lead surgical fastener is dispensed each time the trigger 112 (FIG. 1A) is squeezed. The trailing surgical fasteners may be shifted one position closer to the distal end of the elongated shaft each time the trigger is squeezed or during each firing cycle.

Figure 5:
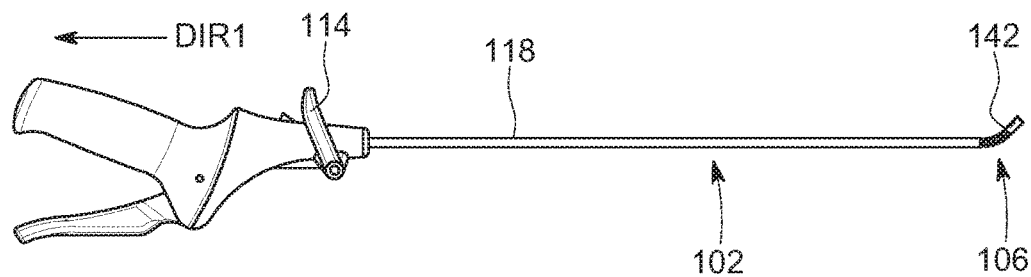
FIGS. 5-7 show an applicator instrument for dispensing surgical fasteners with a distal section of an elongated shaft in an articulated configuration, in accordance with one embodiment.

Referring to FIG. 5, in one embodiment, the distal end 106 of the elongated shaft 102 may be articulated by pivoting the upper end of the articulating lever 114 in the proximal direction DIR1. As the articulation lever 114 is retracted, the outer sheath 118 moves proximally and the exposed segmented member 142 articulates via tension applied to the articulation band 144 (FIG. 3B).

Figure 6:
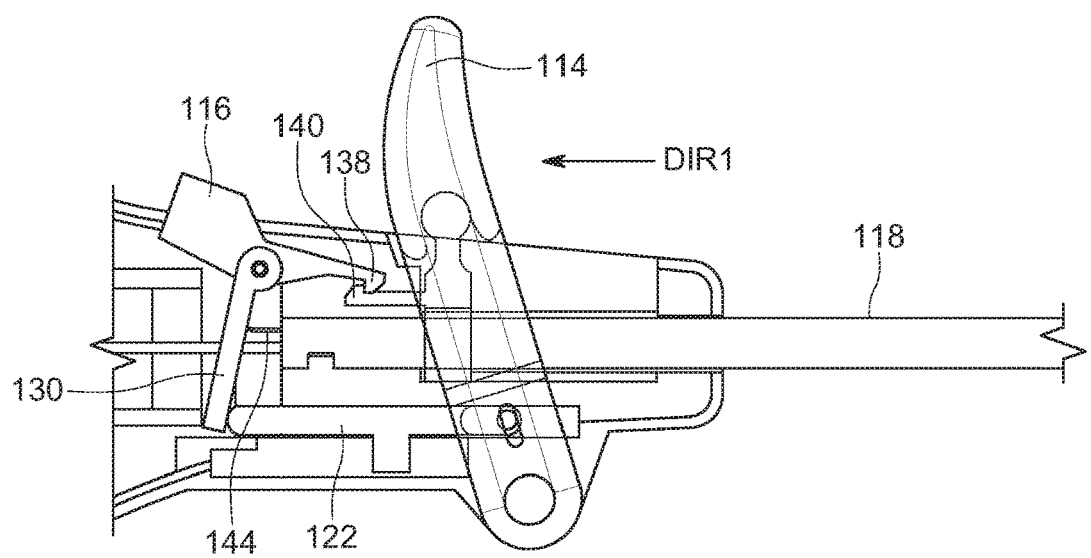

FIG. 6 shows the articulation lever 114 in the retracted, proximal position. As the upper end of the articulation lever 114 moves in the proximal direction designated DIR1, the direct connection between the lever 114 and the outer sheath 118 retracts the outer sheath 118 proximally. As the outer sheath 118 moves proximally, the segmented member 142 is exposed. The pivoting movement of the articulation lever 114 moves the articulation tensioner 122 proximally, which, in turn rotates the lower end of the lever 130 in a clockwise direction for applying tension to the proximal end of the articulation band 144, which is connected with the lever 130 via a pin 146 (FIG. 3B).

Referring to FIG. 6, in one embodiment, as the lever 114 is pulled proximally in the direction DIR1, the catch 140 associated with the lever 114 engages the catch 138 associated with the release 116 for holding the lever 114 and the outer sheath 118 in the retracted position. When it is desired to return the elongated shaft to a straight configuration, the release 116 may be engaged (e.g., depressed) for decoupling the catch 138 of the release 116 from the catch 140 of the lever 114. A return spring (Not shown) preferably moves the articulation tensioner 122, the lever 114, and the outer shaft 118 in the distal direction to release the tension on the articulation band and return the elongated shaft to a straight configuration.

Figure 7:
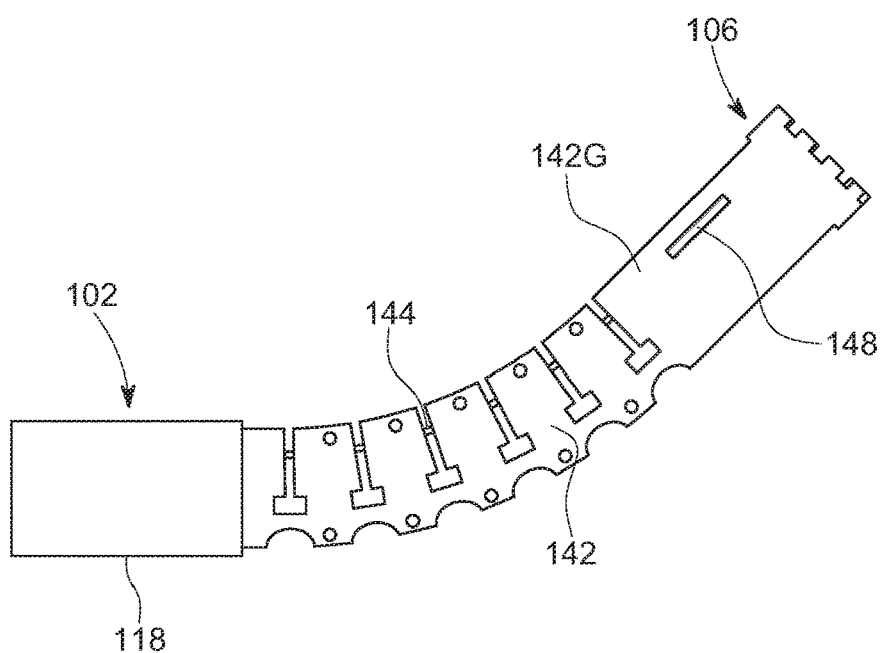

FIG. 7 shows the distal end 106 of the elongated shaft 102 with the shaft in an articulated configuration. In one embodiment, in the articulated configuration, the outer sheath 118 is retracted and the articulation band 144 is under tension. The distal end 148 of the articulation band is affixed to the distal link 142G. The tensioned articulation band 144 pulls the distal link 142G in the proximal direction DIR1, which results in articulation of the segmented member 142. In one embodiment, the individual links may stack against each other, bottoming out to provide rigidity.

Figure 8:
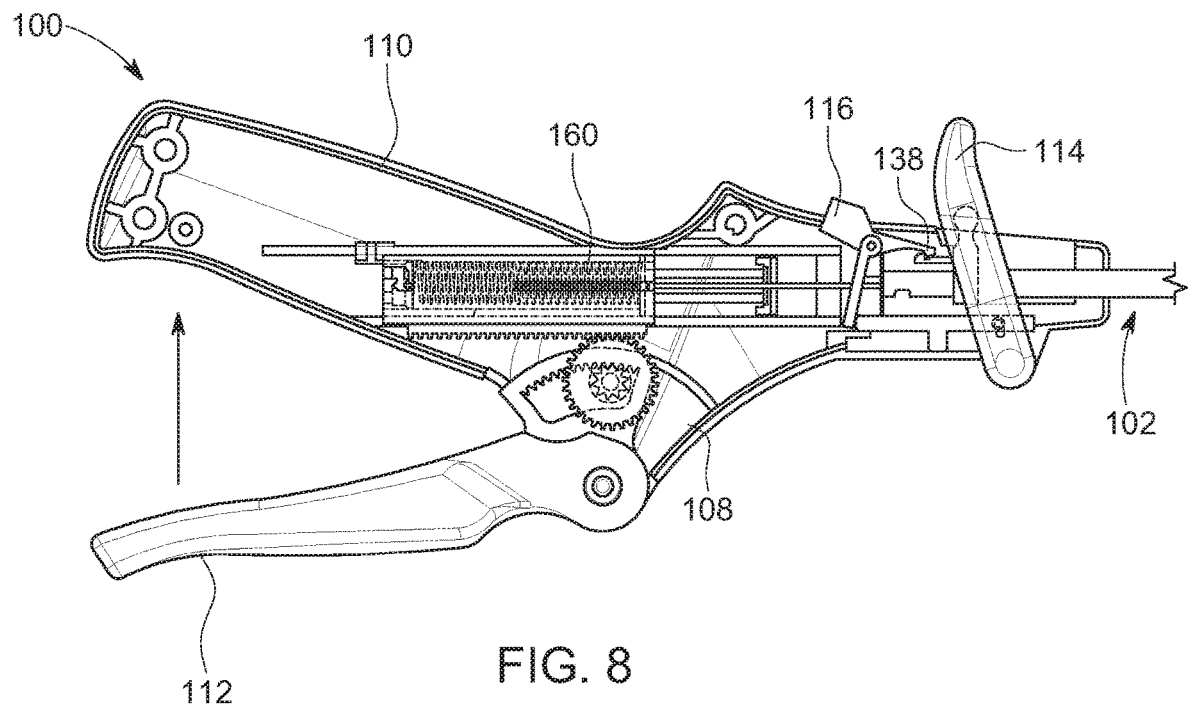
FIG. 8 shows a firing system for an applicator instrument for dispensing surgical fasteners, in accordance with one embodiment.

Referring to FIG. 8, in one embodiment, the applicator instrument 100 is a multi-fire device that contains a plurality of surgical fasteners stored therein as disclosed in commonly assigned U.S. Pat. Nos. 8,579,920; 8,728,098; 8,728,099; 8,894,669; and 8,920,439, the disclosures of which are hereby incorporated by reference herein. In one embodiment, the applicator instrument includes a plurality of surgical fasteners stored in series along the length of the elongated shaft 102. In one embodiment, the firing system includes a pair of flat stampings having tabbed features incorporated therein. The flat stampings may extend from the handle 108 into the elongated shaft 102. One of the flat stampings is stationary for preventing the surgical fasteners from moving proximally within the elongated shaft 102. The other flat stamping cycles in distal and proximal directions each time the trigger 112 is squeezed and then released to facilitate incremental advancement of the surgical fasteners along the length of the elongated shaft 102. In one embodiment, the lead fastener is staged for firing proximal to the articulating segmented member 142 (FIG. 7). In one embodiment, a distal end of a firing rod 152 (FIG. 4C) pilots into the lead surgical fastener and delivers it through a surgical fastener dispensing window at the distal end of the elongated shaft. In one embodiment, the stampings and the firing rod are flexible so that the firing rod may curve to conform to the articulation of the distal end of the elongated shaft while guiding the surgical fasteners along the path defined by the articulated elongated shaft. In one embodiment, a single, lead surgical fastener is dispensed each time the trigger is pulled. During each trigger pull, each of the trailing surgical fasteners are advanced distally toward the distal end of the articulating shaft. In one embodiment, the trigger 112 returns to the open position shown in FIG. 8 when the trigger 112 is released.

Figure 9:
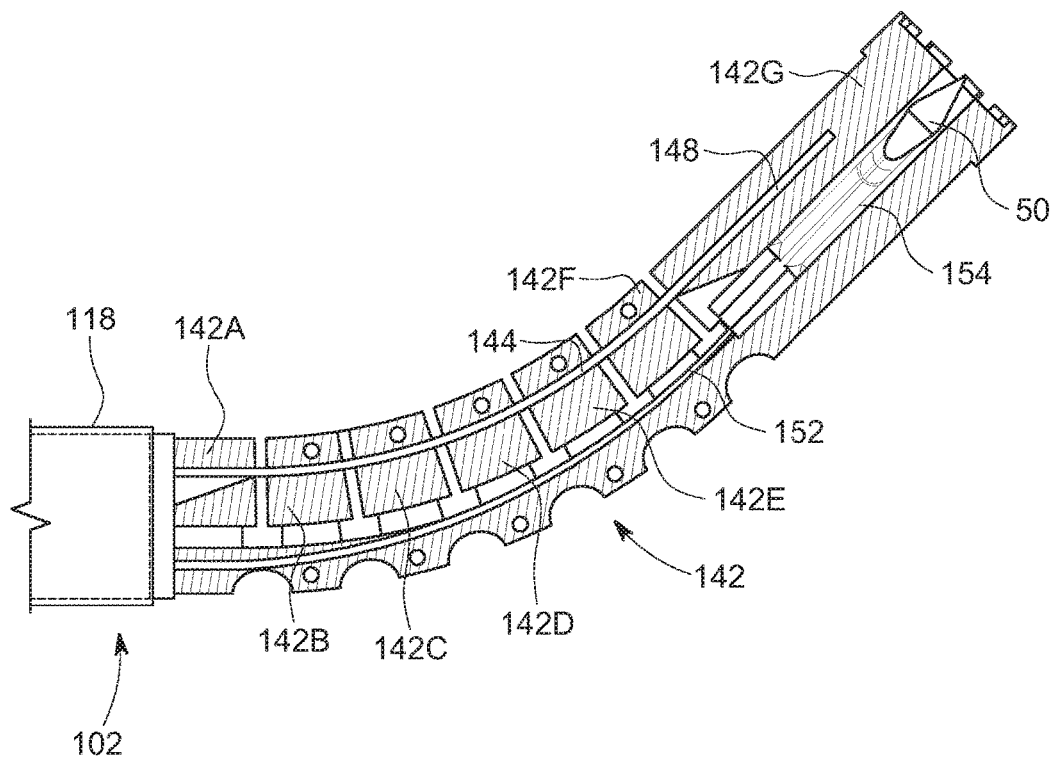
FIG. 9 shows an applicator instrument having an elongated shaft in an articulated configuration, in accordance with one embodiment.

Referring to FIGS. 8 and 9, in one embodiment, the articulation lever 114 is held in a retracted position by the latch 138 on the release 116. As the articulation lever 114 is retracted in a proximal direction, the articulation lever 114, linked with the outer sheath 118 of the elongated shaft 102, retracts the outer sheath 118 relative to the segmented member 142. The retraction of the articulation lever 114 also moves the lever 130 clockwise for applying tension to the articulation band 144 that passes through the upper ends of the proximal links 142A-142F of the segmented member 142. The distal end 148 of the articulation band 144 is affixed to the distal segment 142G of the segmented member 142. The tensioned articulation band 144 pulls the distal link 142G in a proximal direction, which results in articulation of the segmented member 142 into the curve configuration shown in FIG. 9.

During a firing cycle, as the trigger 112 is squeezed toward the handgrip 110, the firing system 160 is activated for driving the firing rod 152 toward the distal end 106 of the elongated shaft 102. An insertion fork 154 is provided at the distal most end of the firing rod 152. A lead surgical fastener 50 is held by the insertion fork 154.

In one embodiment, the applicator instrument 100 may fire surgical fasteners from the distal end of the elongated shaft with the elongated shaft in a straight configuration. In one embodiment, the distal end of the elongated shaft may be articulated by retracting the outer sheath 118 and simultaneously articulating the segmented member 142 via tension applied to the articulation band 144. Thus, surgical fasteners 50 may be dispensed from the distal end 106 of the elongated shaft 102 with the elongated shaft in either a straight configuration or an articulated configuration. Surgical personnel may repeatedly move the elongated shaft 102 back and forth between a straight configuration and an articulated configuration using the articulation lever 114.

Referring to FIG. 10, in one embodiment, a segmented member 242 that is adapted to articulate at a distal end of an elongated shaft includes a cannula having notches formed therein to provide distinct, individual links 242A-242E that may articulate relative to one another. In one embodiment, the individual links 242A-242E have upper ends 270 that are spaced from one another and lower ends 272 that are interconnected with one another via a flexible linkage 274 that extends along the length of the cannula. In one embodiment, an articulation band passes through the individual links 242A-242E adjacent the upper end 270 of the segmented member 242. In one embodiment, the articulation band passes through the links closer to the upper end 270 than the lower end 272. The segmented member 242 is flexible and compliant so that it may be articulated using an articulation band then spring back to a straight configuration when tension on the articulation band is released.

Figure 11A:
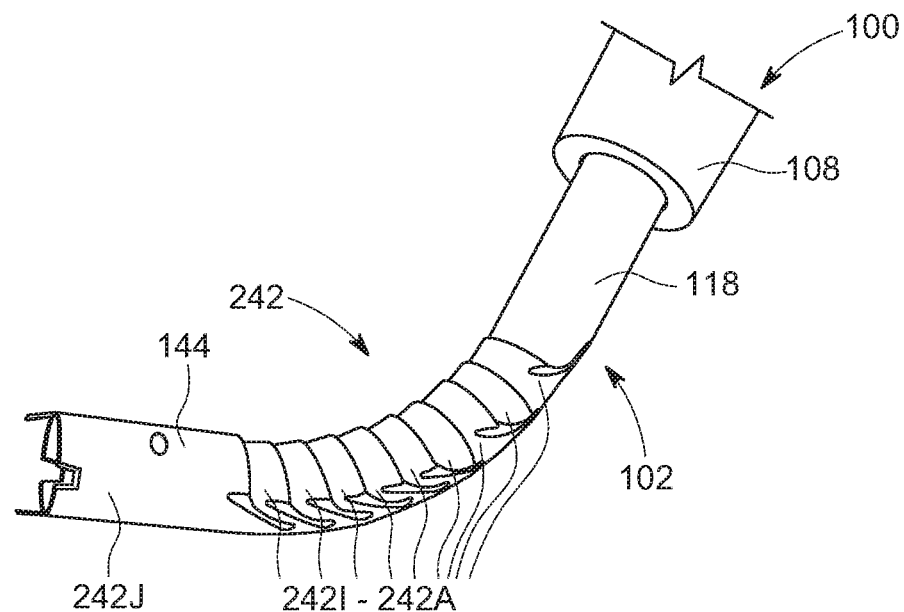
FIGS. 11A and 11B shows the segmented member of FIG. 10 in an articulated configuration, in accordance with one embodiment.
Figure 11B:
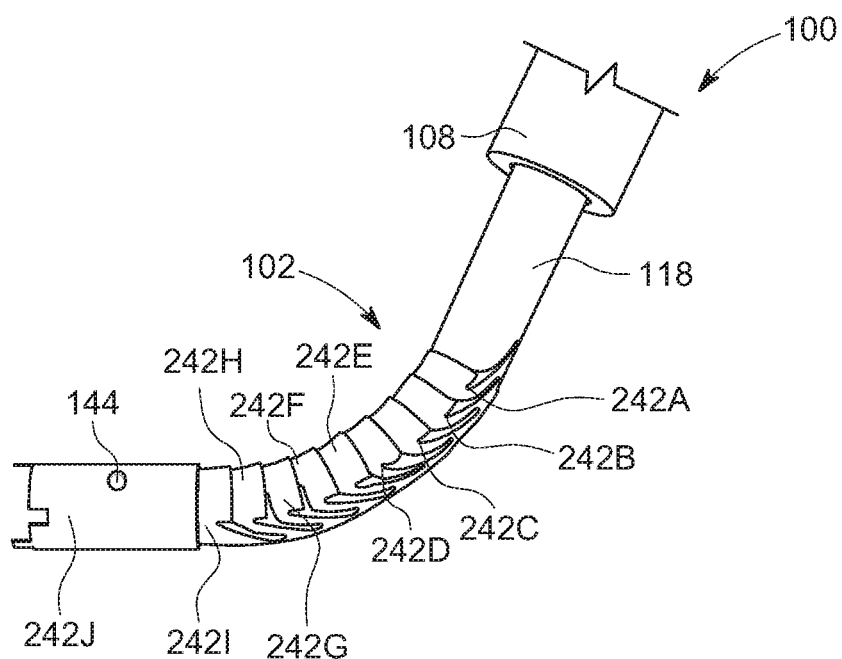

Referring to FIGS. 11A and 11B, in one embodiment, the segmented member 242 formed a distal portion of an applicator instrument 100 including a handle 108 and an outer sheath 118 projecting from a distal end of the handle 108. The applicator instrument 100 preferably includes an articulation band 144 that passes through upper ends of the proximal links 242A-242I of the segmented member 242. The distal end of the articulation band 144 is affixed to the distal link 242J of the segmented member 242. In one embodiment, the applicator instrument 100 includes an articulation lever that may be retracted for retracting the outer sheath 118 of the elongated shaft 102 so as to expose the proximal links 242A-242I of the segmented member 242. As the articulation lever is retracted, tension is applied to the articulation band 144, which articulates the segmented member 242 as shown in FIGS. 11A and 11B.

In one embodiment, the segmented member is adapted to move between a straight configuration and an articulated configuration. The segmented member is preferably flexible so that it may be freely articulated by tension applied through an articulation band. The segmented member is desirably compliant so that it will spring back to a straight configuration when the tension on the articulation band is released. In one embodiment, the segmented member is preferably adapted to move repeatedly between a straight configuration and an articulated configuration, always returning to a straight configuration when the tension on the articulation band is released. In one embodiment, a separate component can be assembled into the segmented member to add spring memory, thereby allowing the segmented member to spring back. Such a member may be made of various materials, including Nitinol.

Figure 12:
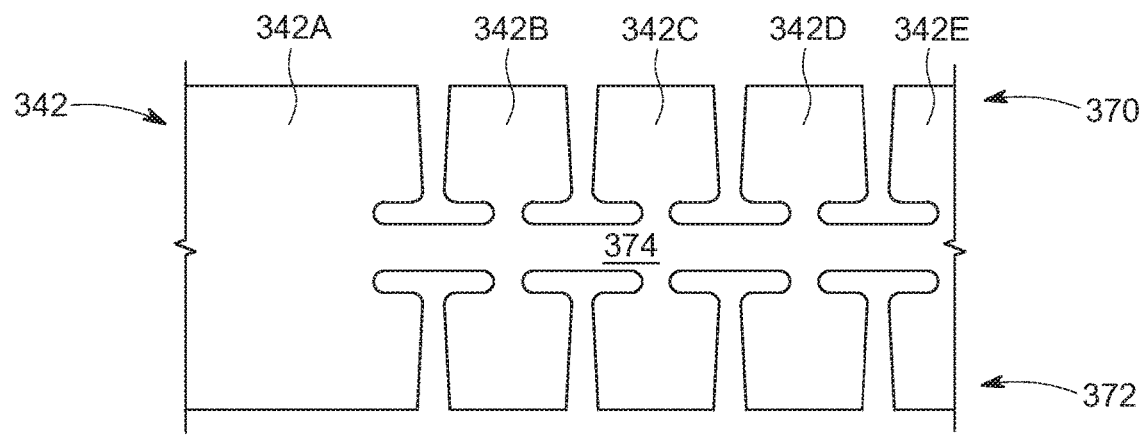
FIG. 12 shows a segmented member for an applicator instrument, in accordance with one embodiment.

Referring to FIG. 12, in one embodiment, the segmented member 342 of an articulating shaft has individual links 342A-342E that are separated from one another by T-shaped notches formed in the top side 370 and the bottom side 372 of the cannula. A flexible elongated linkage 374 extends between the T-shaped notches. In one embodiment, a flexible, elongated linkage 374 may extends on both lateral sides of the cannula.

Figure 13:
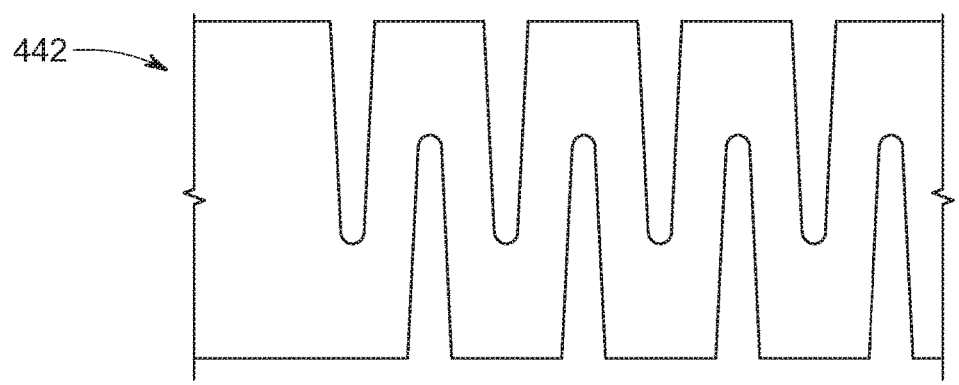
FIG. 13 shows a segmented member for an applicator instrument, in accordance with one embodiment.

Referring to FIG. 13, in one embodiment, a segmented member 442 has individual links that are interconnected with one another. The cannula includes staggered notches formed along the length of the cannula.

Figure 14:
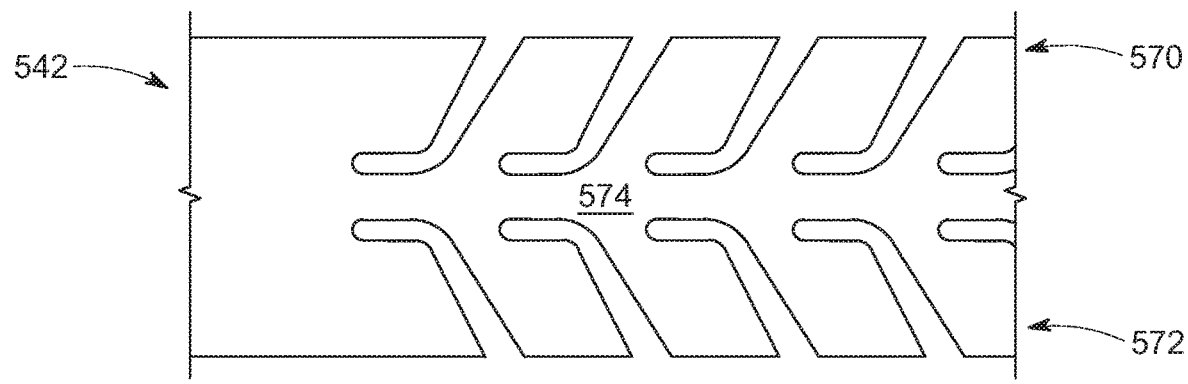
FIG. 14 shows a segmented member for an applicator instrument, in accordance with one embodiment.

Referring to FIG. 14, in one embodiment, a segmented member 552 preferably includes slanted notches formed in the cannula that extend from both the top side 570 and the bottom side 572 of the cannula. An elongated, flexible linkage 574 extends between the slanted notches and along the length of the cannula.

Figure 15A:
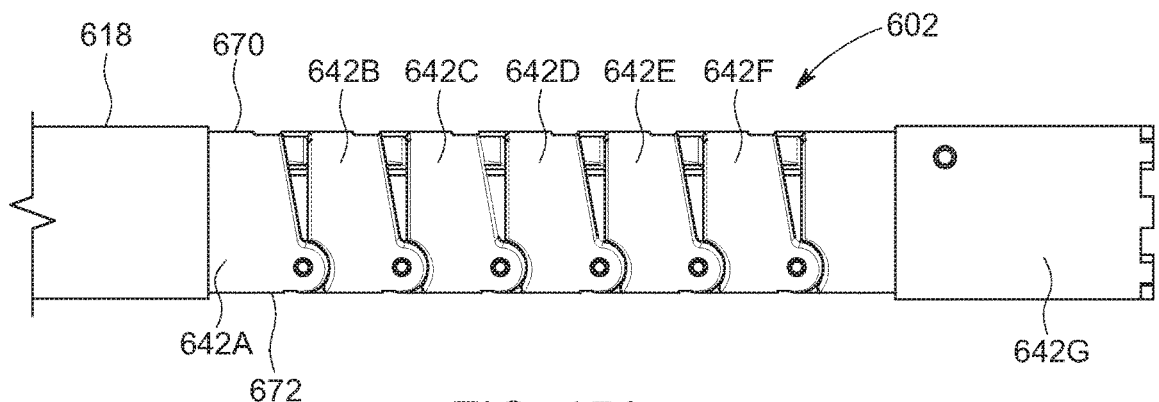
FIGS. 15A and 15B show a segmented member for an applicator instrument including a plurality of links, in accordance with one embodiment.
Figure 15B:
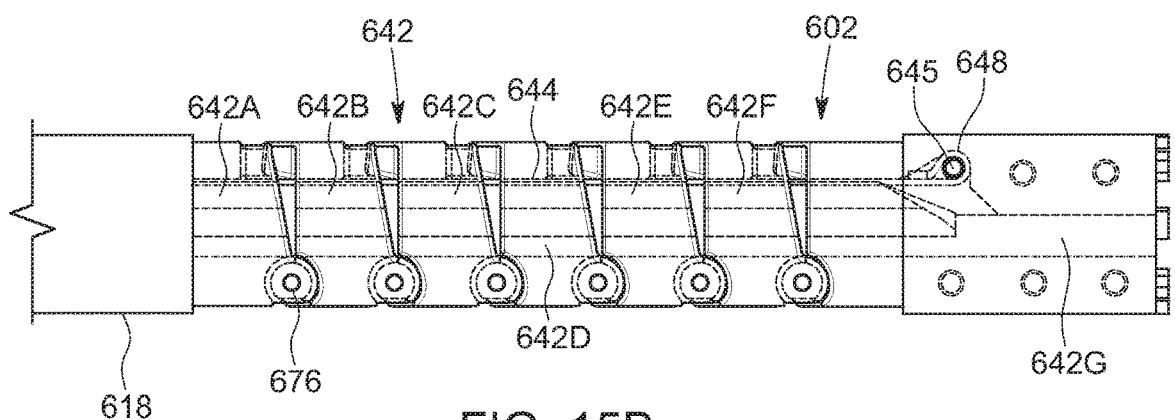

Referring to FIGS. 15A and 15B, in one embodiment, an articulating elongate shaft 602 for an applicator instrument includes an outer sheath 618 that may be retracted in a proximal direction for exposing a segmented member 642 that is adapted to move between a straight configuration and an articulated configuration. In one embodiment, the segmented member 642 includes a plurality of linkages that are hingedly connected to one another. In one embodiment, the segmented member 642 includes a series of proximal links 642A-642F that are hingedly connected to one another along the respective lower ends 672 thereof. The segmented member 642 also includes a distal link 642G that is hingedly connected to the most-distal proximal link 642F. Each of the proximal links 642A-642F have the same length, and the distal link 642G has a length that is greater than the individual lengths of the proximal links 642A-642F.

In one embodiment, an articulation band 644 passes through the proximal links 642A-642F adjacent the respective upper end 670 of the proximal links. The articulation band 644 is free to move distally and proximally relative to the proximal links 642A-642F. The distal most end 648 of the articulation band 644 is affixed to the distal link 642G using a securing pin 645. The respective lower side 672 of the linkages 642A-642G are hingedly connected with one another using pins 676.

Figure 16A:
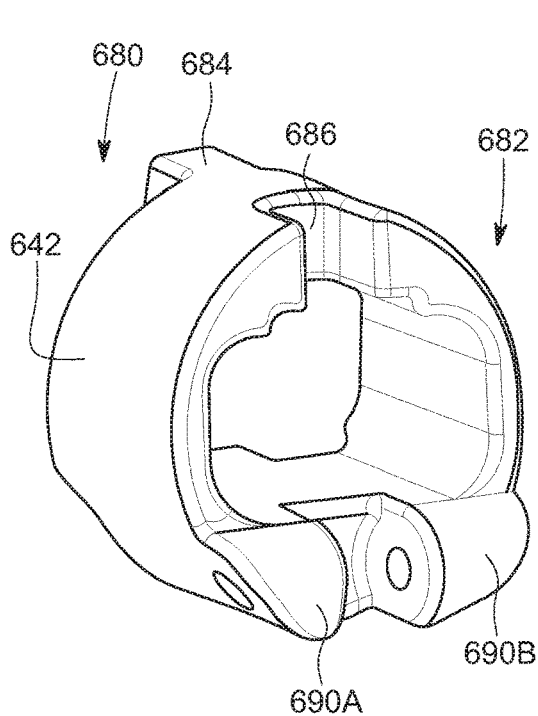
FIGS. 16A and 16B show a link for a segmented member, in accordance with one embodiment.
Figure 16B:
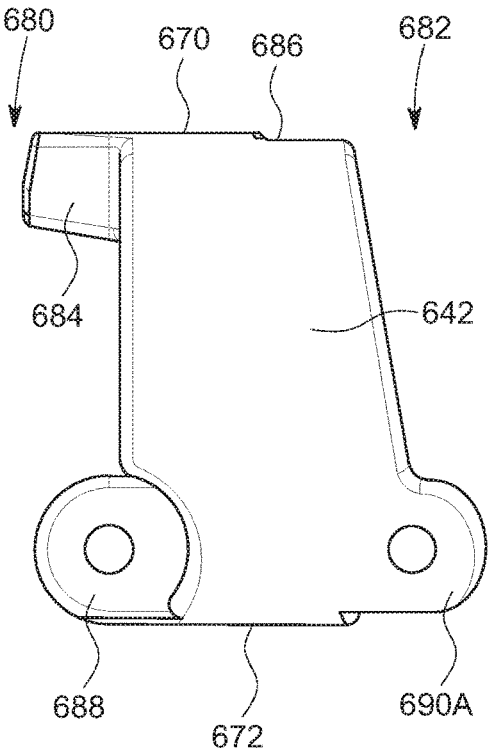

Referring to FIGS. 16A and 16B, in one embodiment, each proximal link 642 has a proximal side 680, a distal side 682, a top side 670, and a bottom side 672. The proximal link 642 includes keying features provided at the top side 670 including a key flange 684 on the proximal side 680 and a key notch 686 on the distal side 682. The bottom side 672 of the proximal link 642B includes a proximal connecting flange 688 at the proximal side 680 and a pair of distal connecting flanges 690A, 690B at the distal side 682. In one embodiment, in order to hingedly interconnect two adjacent linkages 642, the proximal connecting flange 688 of a distal link is disposed between the pair of distal connecting flanges 690A, 690B of a proximal link. In addition, a key flange 684 of a distal link is juxtaposed with a key notch 686 of a proximal link. The articulation band 644 (FIG. 15B) preferably passes through the hingedly connected links adjacent the top sides 670 of the respective proximal links. A pin 676 (FIG. 15B) is preferably passed through the openings of the connection flanges for hingedly connecting the lower ends of the adjacent links to one another.

Referring to FIGS. 17A-17D, in one embodiment, as described herein, an articulation lever may be swung in a proximal direction of an applicator instrument for retracting an outer sheath 618 of an elongated shaft 602 and tensioning an articulation band 644 passing through a segmented member 642 for articulating the segmented member 642. In one embodiment, the segmented member 642 will remain in the articulated position as long as the articulation band 644 remains under tension. In one embodiment, the segmented member 642 may be returned to a straight configuration by moving the articulation lever toward the distal end of the elongated shaft 602, which releases the tension in the articulation band and moves the outer sheath 618 in the distal direction for covering the proximal links 642A-642F and at least partially covering the proximal end of the distal link 642G.

Figure 17A:
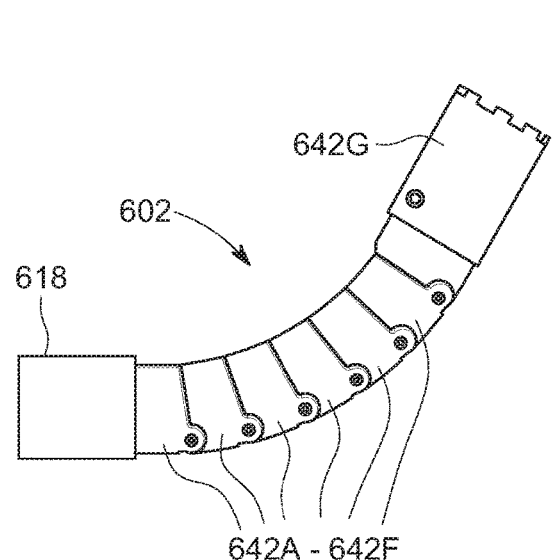
FIGS. 17A-17D show an applicator instrument with an elongated shaft having a segmented member in an articulated configuration, in accordance with one embodiment.
Figure 17B:
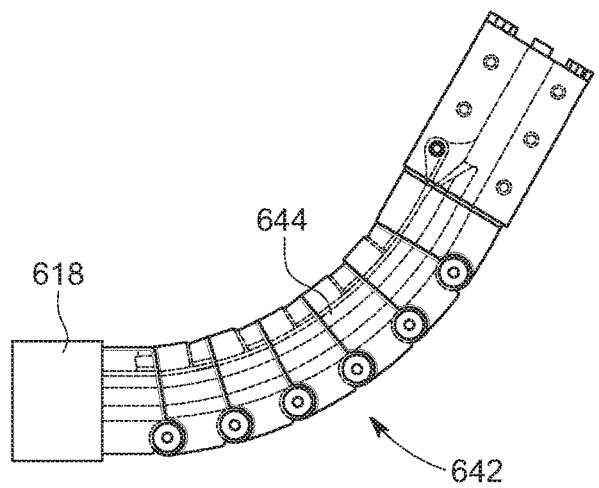
Figure 17C:
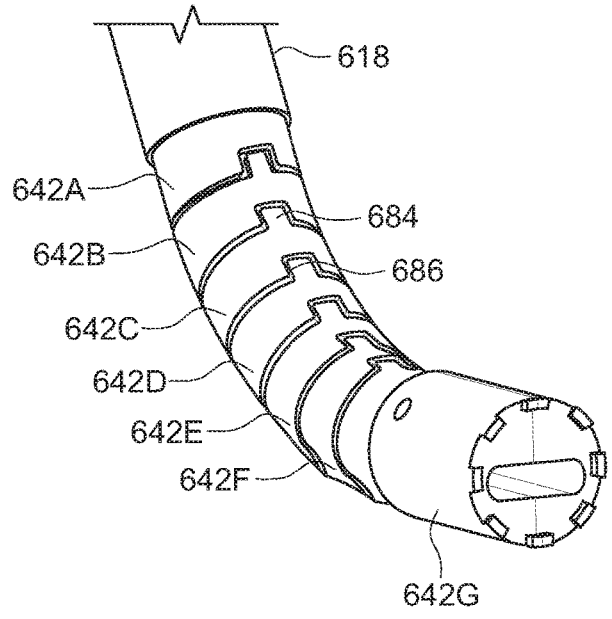

Referring to FIG. 17C, in one embodiment, when the segmented member 642 is articulated, a key flange 684 of a distal link is nested within a key notch 686 of a proximal link. The key flange 684 and the key notch 686 provide a keying feature that prevents rotation of the links relative to one another for enhancing the strength of the segmented member 642.

Figure 17D:
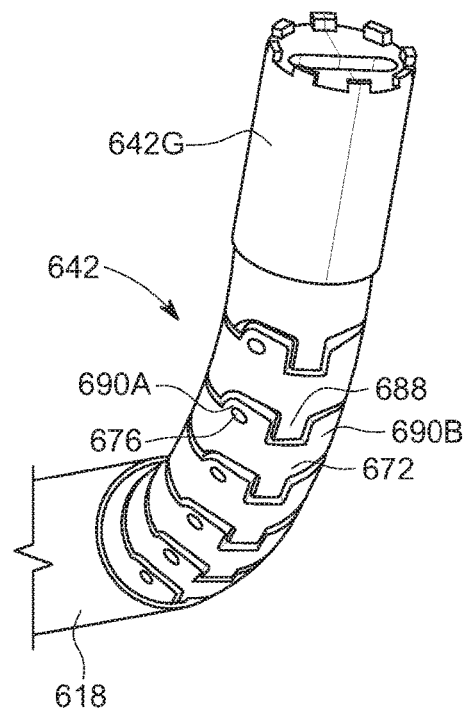

FIG. 17D shows the bottom side of the articulating links of the segmented member 642 when the elongated shaft is in the articulated configuration. The adjacent linkages are interconnected by disposing a connecting flange 688 at the proximal end of a link between the pair of connecting flanges 690A, 690B at the distal end of an adjacent link. A pin 676 desirably passes through aligned openings in the aligned connecting flanges 688, 690A, 690B for forming a hinge connection at the bottom side 672 of adjacent links.

Referring to FIG. 18, in one embodiment, an applicator instrument for dispensing surgical fasteners has an elongated shaft 702 that may move from a straight configuration to an articulated configuration. In one embodiment, the applicator instrument includes substantially the same structure as disclosed above in other embodiments. In one embodiment, the articulating, elongated shaft 702 includes an outer sheath 718 that moves in proximal and distal directions. In one embodiment, the outer sheath 718 may be moved proximally for exposing the segmented member 742 located at the distal end 706 of the elongated shaft. The segmented member 742 includes a series of proximal links 742A-742F that are hingedly connected to one another at the respective lower ends 672 thereof. The segmented member 742 also includes a distal link 742G having a proximal end that is hingedly connected with the distal-most proximal link 742F. In one embodiment, the articulating, elongated shaft 702 includes an articulation band 744 that is disposed over the upper ends 770 of the respective proximal links 742A-742F. The articulation band 744 has a distal end that is affixed to the distal link 742G via a pin 745.

Referring to FIGS. 19A-19D, in one embodiment, when an articulation lever of an applicator is moved in a proximal direction, the outer sheath 718 of the elongated shaft 702 is retracted for exposing the proximal and distal links of the segmented member 742. Proximal movement of the articulation lever also increases tension on the articulation band 744. The tension applied to the articulation band 744 pulls the distal link 742G is the proximal direction DIR1, which articulates the segmented member 742. The applicator instrument desirably includes a firing system having a firing rod with a distal end that is adapted to push a surgical fastener through the articulated segmented member 742. The firing rod is desirably flexible so that it may dispense surgical fasteners with the elongated shaft 702 in both a straight configuration and the articulated figuration shown in FIGS. 19A-19D. The segmented member 742 will remain in the articulated configuration as long as tension is applied to the articulation band 744.

In one embodiment, when it is desired to return the elongated shaft 702 to a straight configuration, the articulation lever may be moved toward the distal end of the elongated shaft for moving the outer sheath 718 distally and simultaneously reducing the tension in the articulation band 744. In one embodiment, when the outer sheath 718 moves distally, the leading end 719 of the outer sheath 718 will slide over the articulation band 744 so as to protect the top sides 770 of the links 742A-742G from any sharp edges on the outer sheath 718.

Referring to FIG. 20A, in one embodiment, an applicator instrument 800 for dispensing surgical fasteners includes an elongated shaft 802 having an outer sheath 818 that is adapted to move in distal and proximal directions, and a segmented member 842 that is adapted to articulate when the outer sheath 818 is retracted and tension is applied to an articulation band 844. The applicator instrument 800 includes a firing system having an anti-backup stamping 892 for preventing the surgical fasteners 50 from moving proximally within the elongated shaft 802, a surgical fastener advancer 894, a spring element 896 for shifting a lead surgical fastener 50A from an advancing track to a firing track, and a firing rod 852 adapted to dispense the lead surgical fastener 856A from the distal end 806 of the elongated shaft 802. In one embodiment, the advancer 894, the anti-backup stamping 892, and the spring element 896 are disposed within the outer sheath 818 portion of the elongated shaft 802 and do not extend into the segmented member 842 that articulates.

Referring to FIG. 20B, after the lead surgical fastener 50A has been shifted into the firing channel, the distal end of the firing rod 852 engages the lead surgical fastener 50A. FIG. 20C shows a later stage of a firing operation with the firing rod 852 fully advanced to a distal-most position for dispensing the lead surgical fastener 50A from the distal end 806 of the elongated shaft 802.

Figure 21A:
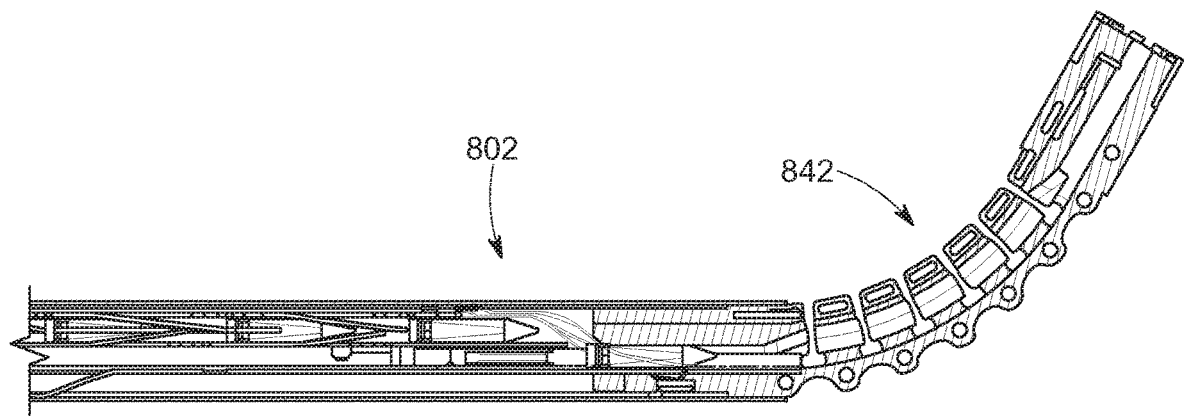
FIGS. 21A and 21B show the applicator instrument of FIGS. 20A-20C with the segmented member in an articulated configuration.
Figure 21B:
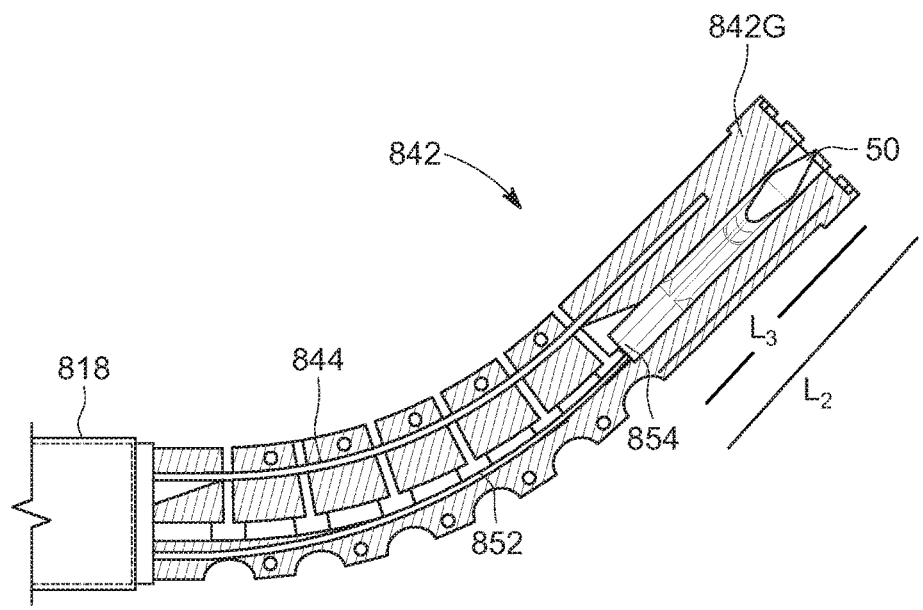

In FIGS. 20A-20O, the elongated shaft 802 is in a straight configuration for firing surgical fasteners from the distal end 806 of the elongated shaft 802. FIGS. 21A-2B show the elongated shaft 802 in an articulated configuration for firing surgical fasteners from the distal end of the elongated shaft with the segmented member 842 in the articulated or curved configuration shown therein. Referring to FIG. 21B, the outer sheath 818 has been retracted to expose the segmented member 842. Tension is applied to the articulation band 844 for articulating the segmented member 842. In one embodiment, the firing rod 852 is flexible so that it may curve as it passes through the articulated section at the distal end of the elongated shaft. As the firing rod 852 advances distally through the articulated, segmented member 842, the firing rod 852 curves to follow the curved firing path formed in the segmented member 842. The distal link 842G at the distal-most end of the segmented member 842 has a length $L_2$ that preferably equal to or greater than the combined length $L_3$ of the insertion fork 854 and the surgical fastener 856 loaded onto the insertion fork 854, which provides stability for the insertion fork and the surgical fastener as the surgical fastener 50 is pushed into tissue or a medical implant (e.g., a surgical mesh).

Figure 22A:
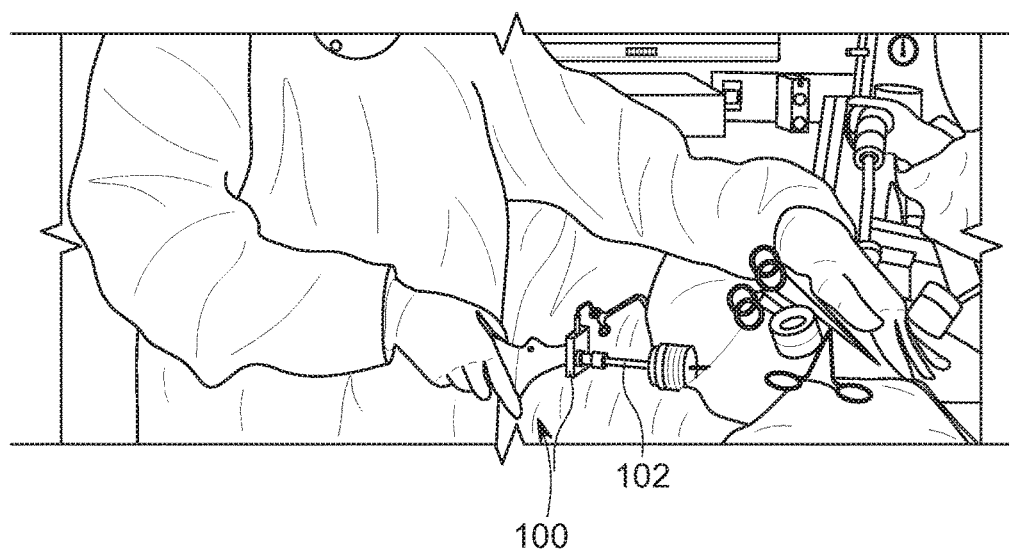
FIGS. 22A and 22B show a surgical procedure performed using an applicator instrument having a segmented member, in accordance with one embodiment.
Figure 22B:
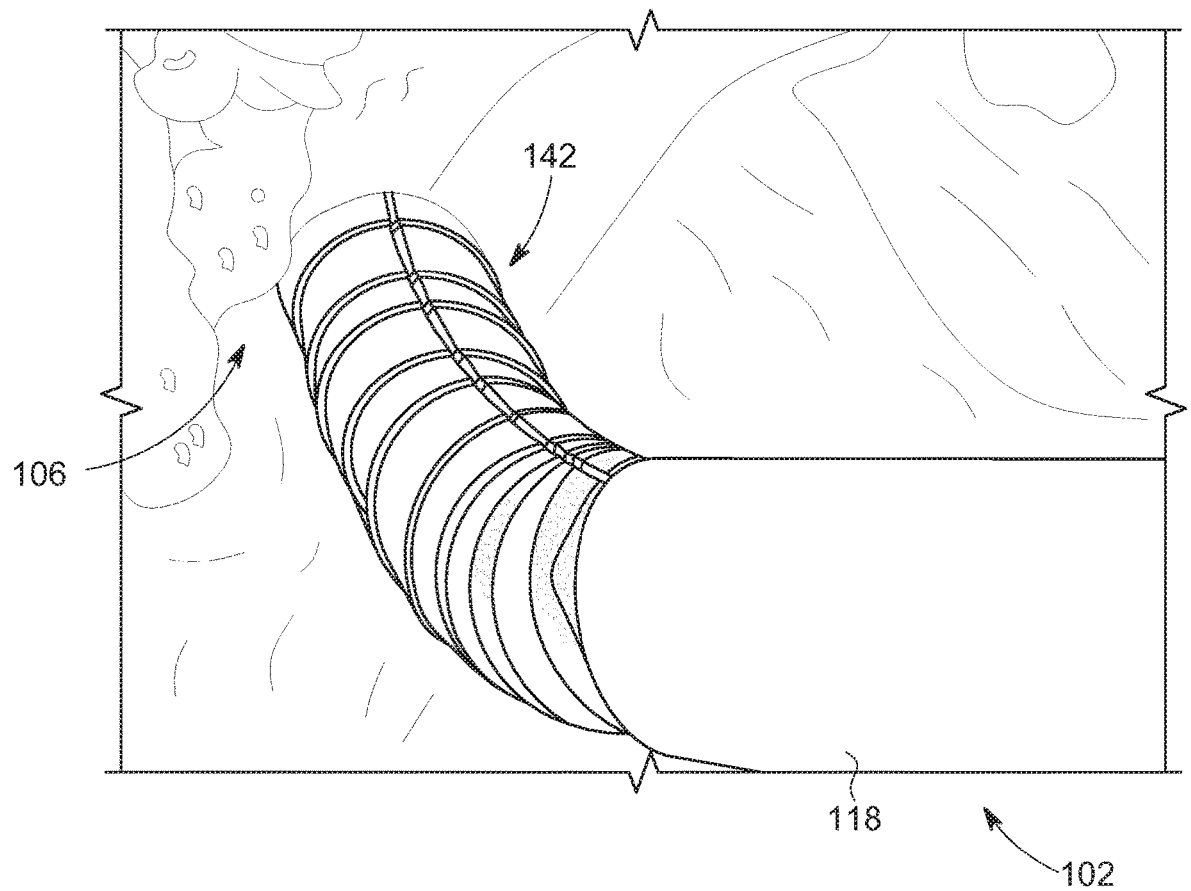
Figure 23:
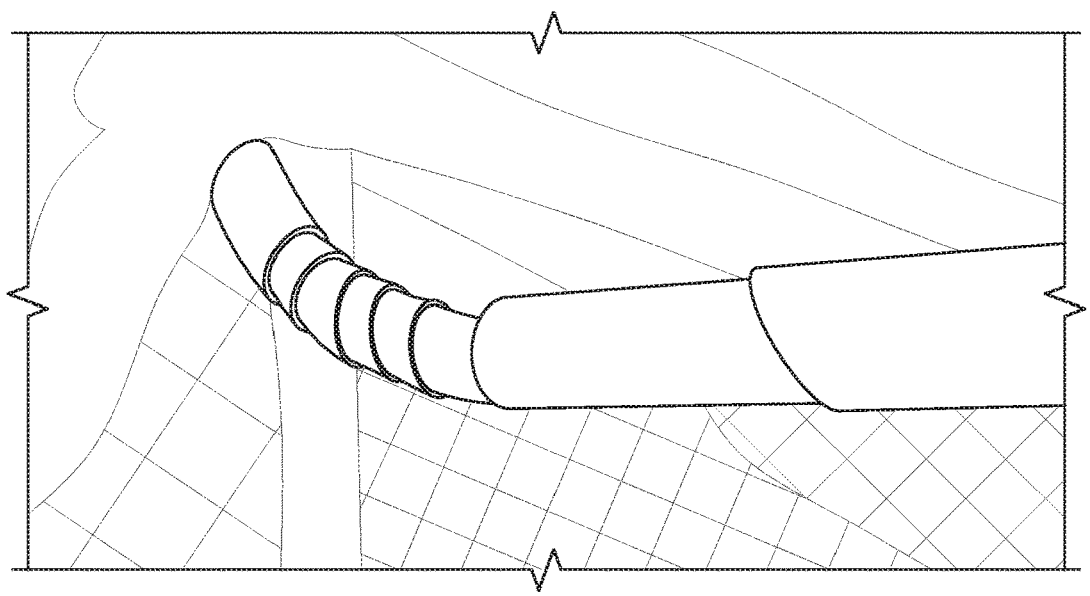
FIG. 23 shows a surgical procedure performed using an applicator instrument having a segmented member, in accordance with one embodiment.
Figure 24:
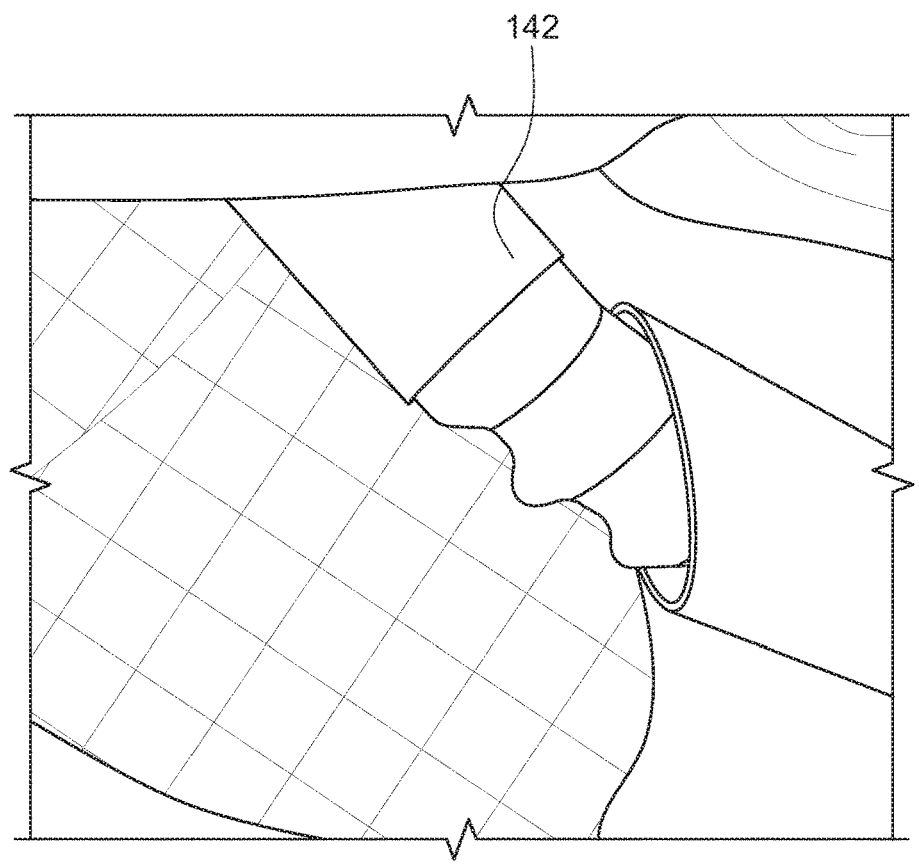
FIG. 24 shows a surgical procedure performed using an applicator instrument having a segmented member, in accordance with one embodiment.

Referring to FIG. 22A, in one embodiment, the applicator instrument 100 may be used during a surgical procedure such as a hernia repair procedure. The elongated shaft 102 is advanced through a port opening of a surgical device. FIG. 22B shows the distal end 106 of the elongated shaft 102 at a surgical site. During a surgical procedure, the outer sheath 118 may be retracted relative to the segmented member 142. Tension may be applied to an articulation band that passes through the segmented member for articulating the segmented member 142. FIG. 23 shows the applicator instrument 100 of FIGS. 22A and 22B used for securing mesh during a hernia repair procedure. FIG. 24 shows how a short section of the segmented member 142 may be articulated for securing a proximal section of surgical mesh to tissue.

Figure 25A:
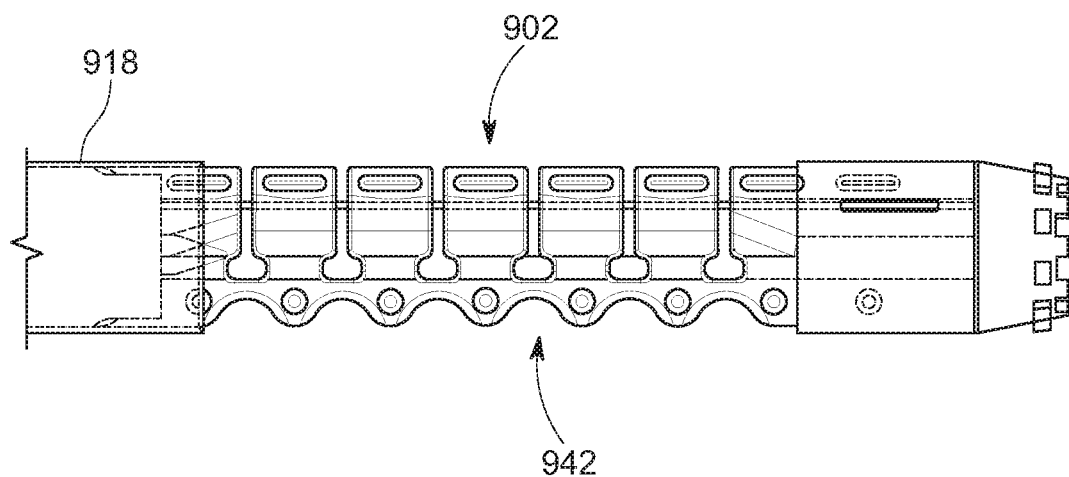
FIGS. 25A and 25B show an applicator instrument having an elongated shaft with a segmented member that is moveable between a straight configuration to an articulated configuration, in accordance with one embodiment.
Figure 25B:
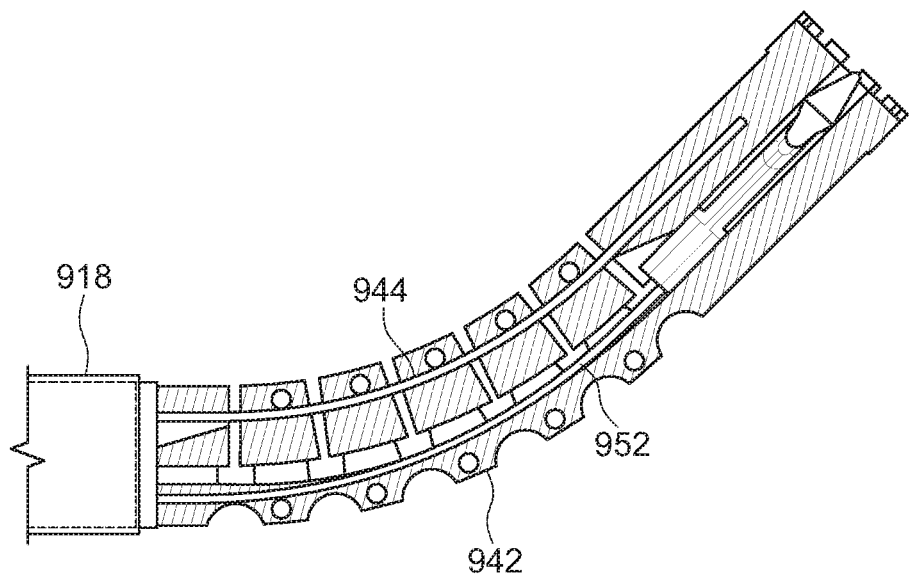

In one embodiment, retracting the outer sheath and articulating the segmented member may be accomplished during separate, distinct steps. Referring to FIGS. 25A and 25B, in one embodiment, the outer sheath 918 of an elongated shaft 902 is retracted for exposing the segmented member 942 while the segmented member 942 maintains a straight configuration. After the outer sheath 918 has been retracted, and during a separate, distinct step, tension may be applied to the articulation band 944 for articulating the segmented member 942 into the curved configuration shown in FIG. 25B. Thus, in one embodiment, an applicator instrument uses a first distinct step for retracting the outer sheath 918 and a separate distinct step for articulating the segmented member 942. The applicator instrument desirably includes a firing rod 952 that is flexible and compliant so that it may pass through the segmented member 942 when it is in both the straight configuration of FIG. 25A and the articulated configuration of FIG. 25B.

Figure 26A:
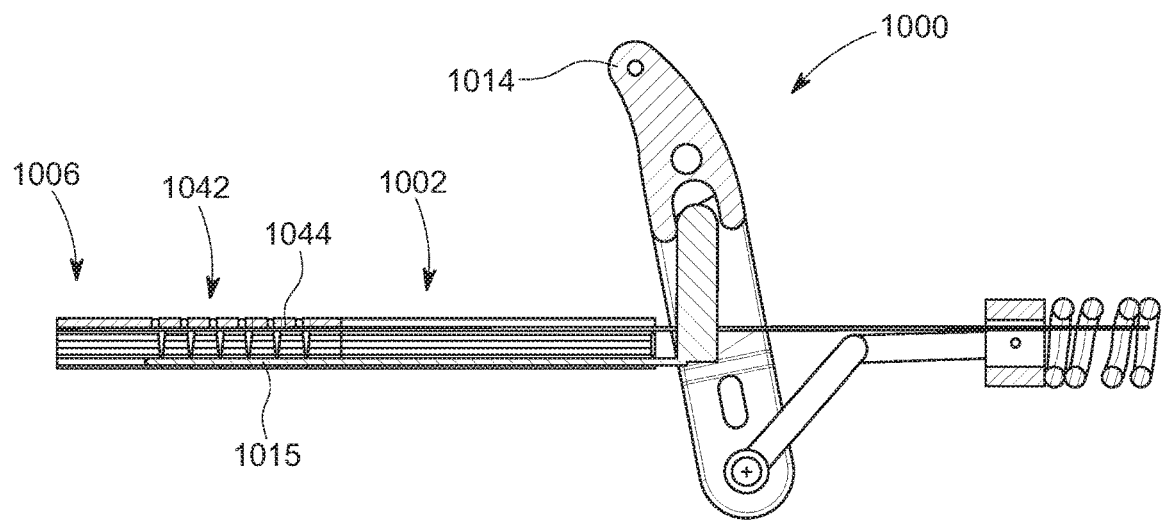
FIGS. 26A and 26B show an applicator instrument having an elongated shaft with a segmented member that is moveable between a straight configuration to an articulated configuration, in accordance with one embodiment.

Referring to FIG. 26A, in one embodiment, an applicator instrument includes an elongated shaft 1002 having distal end 1006 that is adapted to be articulated. The elongated shaft 1002 preferably includes a segmented member 1042 having proximal links and a distal link. The applicator instrument 1000 desirably includes an articulation band 1044 that is connected with an articulation lever 1014. The applicator instrument 1000 also preferably includes a rigid rod 1015 that is linked with the articulation lever 1014.

In FIG. 26A, the articulation lever 1014 is in a distal position so that the rigid rod 1015 is extended through the links of the segmented member 1042 and so that no tension is applied to the articulation band 1044.

Figure 26B:
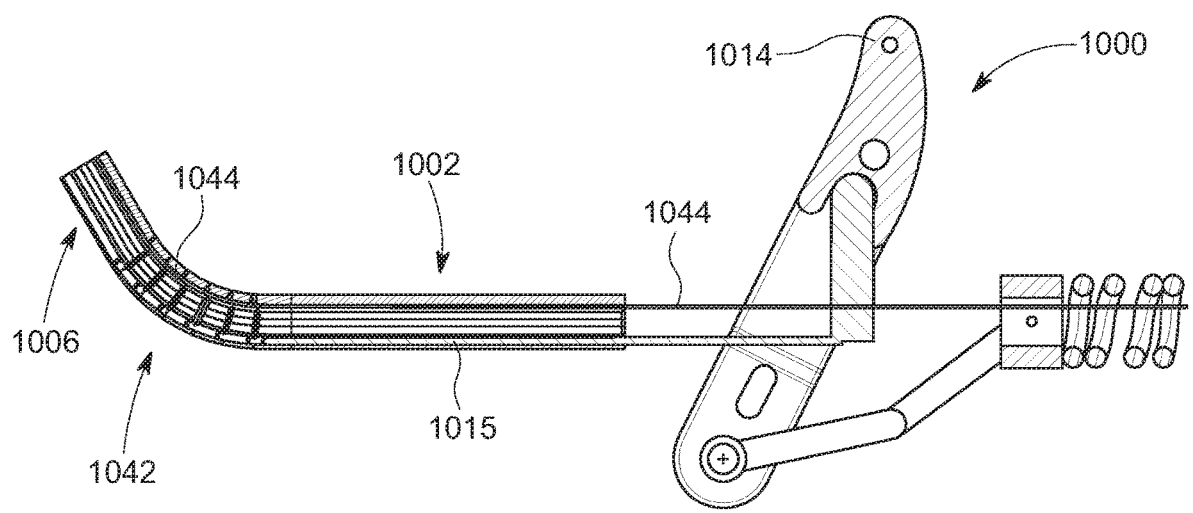

In FIG. 26B, the articulation lever 1014 is retracted in a proximal direction which, in turn retracts the rigid rod 1015 from the links of the segmented member 1042. Simultaneously, as the lever 1014 is moved proximally, tension is applied to the articulation band 1044 for articulating the segmented member 1042. The applicator instrument may be utilized for dispensing surgical fasteners from the distal end 1006 of the elongated shaft 1002 with the shaft in either the straight or articulated/curved configuration. In order to return the elongated shaft 1002 to the straight configuration of FIG. 26A, the lever 1014 is desirably advanced in a distal direction toward the distal end 1006 of the elongated shaft 1002 to extend the rigid rod 1015 into the links of the segmented member 1042 and lessen the tension on the articulation band 1044 so that the links of the segmented member may spring back to the straight configuration. In one embodiment, a spring is connected between the lever 1014 and the articulation band 1044 to prevent over-tensioning of the articulation band 1044.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An applicator instrument for dispensing surgical fasteners comprising:
   an elongated shaft having a proximal shaft section and a distal shaft section, said proximal shaft section including an outer sheath and said distal shaft section including a segmented member disposed within a distal end of said outer sheath, wherein said segmented member is moveable between a straight configuration and an articulated configuration;

a handle secured to said proximal shaft section;

an actuator provided on said handle and being coupled with said outer sheath for moving said outer sheath in proximal and distal directions along an axis;

an articulation band disposed within said outer sheath that extends from said handle to said segmented member, said articulation band having a proximal end coupled with said actuator and a distal end attached to said segmented member, wherein said actuator is moveable in a first direction for moving said outer sheath in a proximal direction along the axis to expose a portion of said segmented member and applying tension to said articulation band for moving said segmented member into the articulated configuration, and wherein said actuator is moveable in a second, opposite direction for moving said outer sheath in a distal direction along the axis to cover the portion of said segmented member and to release the tension on said articulation band to enable said segmented member to return to the straight configuration;

said segmented member comprising a series of separate, independent links that are interconnected and movable relative to one another as said segmented member moves between the articulated configuration and the straight configuration, wherein each said link has a proximal side that is closer to a proximal end of said elongated shaft, a distal side that is closer to a distal end of said elongated shaft, a first lateral side having a tongue and groove structure, and a second lateral side, opposite the first lateral side, having a hinge connection, wherein the hinge connections of said links are only at the second lateral sides of said links.

2. The applicator instrument as claimed in claim 1, wherein said segmented member comprises plastic or metal.

3. The applicator instrument as claimed in claim 1, wherein the first lateral sides of said links define upper ends of said links and the second lateral sides of said links define lower ends of said links, and wherein the hinge connections of said links are only at the lower ends of said links.

4. The applicator instrument as claimed in claim 1, wherein said links comprise a distal link that is located at the distal end of said elongated shaft and a series of proximal links that are proximal to said distal link, and wherein the distal end of said articulation band is affixed to said distal link of said segmented member.

5. The applicator instrument as claimed in claim 4, wherein said articulation band passes through said proximal links.

6. The applicator instrument as claimed in claim 4, wherein said articulation band passes above said proximal links.

7. The applicator instrument as claimed in claim 4, wherein said proximal links have a first length and said distal link has a second length that is greater than the first length.

8. The applicator instrument as claimed in claim 1, wherein the second lateral side of each said link includes a proximal connecting flange at the proximal side of said link and a pair of distal connecting flanges at the distal side of said link, wherein the proximal connecting flange of a distal one of said links is disposed between the pair of distal connecting flanges of a proximal one of said links for hingedly interconnecting the proximal and distal ones of said links to one another.

9. The applicator instrument as claimed in claim 8, further comprising a pin passing through openings of the proximal connecting flange and the pair of distal connecting flanges of the proximal and distal ones of said links for hingedly interconnecting the proximal and distal ones of said links to one another.

10. The applicator instrument as claimed in claim 1, further comprising:

a firing system disposed in said handle, said firing system including a firing rod that extends through said proximal and distal shaft sections of said elongated shaft, wherein said firing rod moves in distal and proximal directions during a firing cycle;

a trigger coupled with said handle for activating said firing system.

11. The applicator instrument as claimed in claim 10, further comprising a plurality of surgical fasteners, wherein a leading one of said surgical fasteners is dispensed during each said firing cycle.

12. The applicator instrument as claimed in claim 10, wherein said firing rod has a distal end that is flexible for bending when said segmented member is in the articulated configuration.

13. The applicator instrument as claimed in claim 12, wherein said distal end of said firing rod is substantially straight when said segmented member is in the straight configuration and is bent when said segmented member is in the articulated configuration.

14. An applicator instrument for dispensing surgical fasteners comprising:

an elongated shaft having a proximal shaft section and a distal shaft section, said proximal shaft section including a rigid outer sheath and said distal shaft section including a segmented member disposed within a distal end of said outer sheath;

said segmented member comprising a series of separate, independent links that are flexibly interconnected for enabling said segmented member to move between a straight configuration and an articulated configuration;

a handle secured to said proximal shaft section;

an actuator provided on said handle and coupled with said outer sheath for moving said outer sheath in proximal and distal directions along an axis;

an articulation band disposed within said outer sheath that extends from said handle to said segmented member, said articulation band having a proximal end coupled with said actuator and a distal end attached to a distal-most one of said links, wherein said actuator is moveable in a first direction for moving said outer sheath in a proximal direction along the axis to expose said links of said segmented member and applying tension to said articulation band for moving said segmented member into the articulated configuration, and wherein said actuator is moveable in a second, opposite direction for moving said outer sheath in a distal direction along the axis to cover said links of said segmented member and release the tension on said articulation band for enabling said segmented member to return to the straight configuration;

wherein each said link has a proximal side that is closer to a proximal end of said elongated shaft, a distal side that is closer to a distal end of said elongated shaft, a first lateral side having a tongue and groove structure, and a second lateral side, opposite the first lateral side, having a hinge connection, and wherein the hinge connections of said links are only at the second lateral sides of said links.

15. The applicator instrument as claimed in claim 14, wherein the first lateral sides of said links define upper ends of said links and the second lateral sides of said links define lower ends of said links, and wherein the hinge connections of said links are only at the lower ends of said links.

16. The applicator instrument as claimed in claim 14, wherein the second lateral sides of said links are hingedly connected with one another using pins that pass through openings of connecting flanges of adjacent ones of said links.

17. The applicator instrument as claimed in claim 14, further comprising:
- a firing system disposed in said handle, said firing system including a firing rod that extends through said proximal and distal shaft sections of said elongated shaft, wherein said firing rod moves in distal and proximal directions during a firing cycle, and wherein said firing rod has a distal end that is flexible for bending when said segmented member is in the articulated configuration;
- a trigger coupled with said handle for activating said firing system.

18. The applicator instrument as claimed in claim 17, further comprising a plurality of surgical fasteners disposed in said elongated shaft, wherein a leading one of said surgical fasteners is dispensed during each said firing cycle.

* * * * *